United States Patent
Steinkasserer et al.

(10) Patent No.: US 9,822,377 B2
(45) Date of Patent: Nov. 21, 2017

(54) MUTANT CD83 PROMOTER AND USE THEREOF

(75) Inventors: Alexander Steinkasserer, Marloffstein (DE); Marcello Stein, Nürnberg (DE); Thomas Werner, München (DE); Ilka Knippertz, Nürnberg (DE)

(73) Assignee: FRIEDRICH-ALEXANDER-UNIVERISTÄT ERLANGEN-NÜRNBERG, Erlangen (DE)

( * ) Notice: Subject to any disclaimer, the term of this patent is extended or adjusted under 35 U.S.C. 154(b) by 308 days.

(21) Appl. No.: 14/113,844

(22) PCT Filed: Apr. 27, 2012

(86) PCT No.: PCT/EP2012/057760
§ 371 (c)(1),
(2), (4) Date: Oct. 25, 2013

(87) PCT Pub. No.: WO2012/146713
PCT Pub. Date: Nov. 1, 2012

(65) Prior Publication Data
US 2014/0050748 A1     Feb. 20, 2014

(30) Foreign Application Priority Data
Apr. 29, 2011   (EP) ..................................... 11164344

(51) Int. Cl.
*C12N 15/85*       (2006.01)
*C12N 15/86*       (2006.01)

(52) U.S. Cl.
CPC ............ *C12N 15/85* (2013.01); *C12N 15/86* (2013.01); *C12N 2710/10041* (2013.01)

(58) Field of Classification Search
None
See application file for complete search history.

(56) References Cited

PUBLICATIONS

Berchtold et al; "The human dendritic cell marker CD83 maps to chromosome 6p23"; Ann. Hum. Genet. (1999), 63, pp. 181-183.
Lechmann et al; "CD83 s a dimer: Comparative analysis of monomeric and dimeric isoforms"; Biochemical and Biophysical Research Communications 329 (2005) pp. 132-139.
Ohta et al; "Homologs of CD83from Elasmobranch and Teleost Fish"; The Journal of Immunology; (2004) 173, pp. 4553-4560.
Berchtold et al; "Cloning and Characterization of the Promoter Region of the Human CD83 Gene"; Immunobiol. (2002) 205; pp. 231-246.
McKinsey et al; "Transriptionfactor NF-κB regulates inducible CD83 gene expression in activated T lymphocytes"; Molecular Immunology 37 (2000) pp. 783-788.
Dudziak et al; "Latent Membrance Protein 1 of Epstein-Barr Virus Induces CD83 by the NF-κB Signaling Pathway"; Journal of Virology, (Aug. 2003) pp. 8290-8298.
Twist et al; "The mouse Cd83 gene: structure, domain, organization, and chromosome localization"; Immunogenetics (1998) 48: pp. 383-393.
Knippertz; "Genetic and physical modification of human moncyte-derived dendritic cells in order to improve vaccination protocois"; Thesis Universität Erlangen-Nürnberg, (2008).

*Primary Examiner* — Gerald R Ewoldt
(74) *Attorney, Agent, or Firm* — Norris McLaughlin & Marcus, P.A.

(57) ABSTRACT

The present invention provides a mutant CD83 promoter comprising the promoter/enhancer regions of human CD83 promoter and being dendritic cell-specific, and the use thereof, specifically for the treatment or prevention of diseases or medical conditions related to malignancy, autoimmunity or prevention of transplant rejections.

13 Claims, 22 Drawing Sheets

Figure 1:
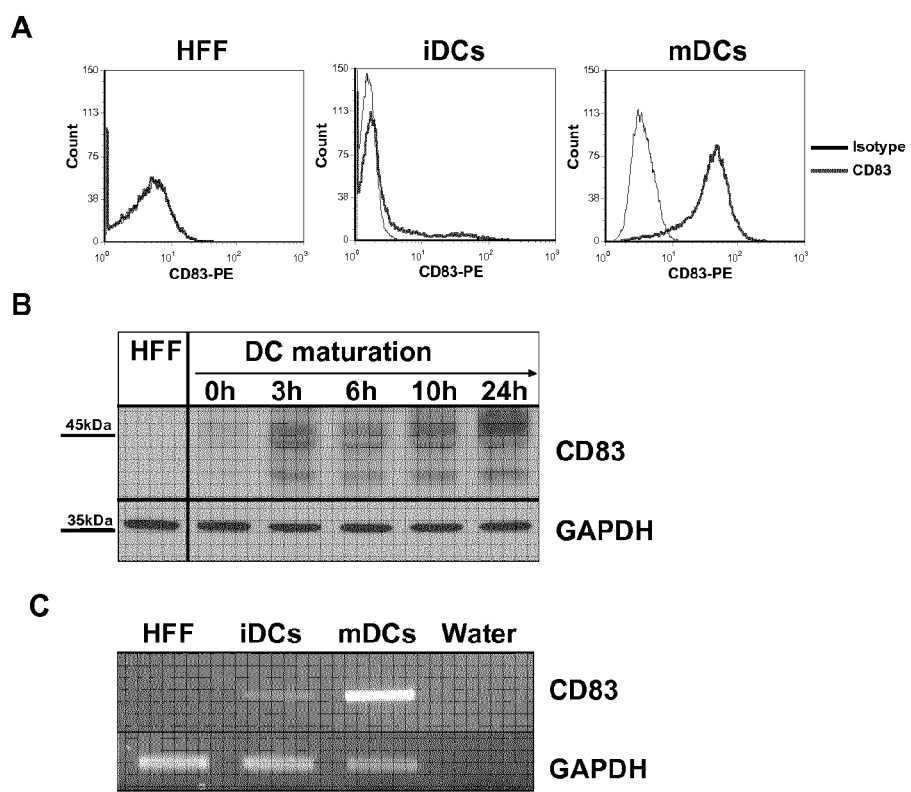

| | | XS52 | NIH3T3 | HeLa |
|---|---|---|---|---|
| sense and antisense 5'- ▭ -3' | Fragment C bp 1-2220 | + + | - - - | - - - |
| | C1 bp 1-1720 | + + | - - - | - - - |
| | C2 bp 1-1010 | + + + | - - - | - - - |
| | C3 bp 1-525 | + + + | - - - | - - - |
| | C4 bp 501-2220 | - - - | - - - | - - - |
| | C5 bp 501-1220 | - - - | - - - | - - - |
| | C6 bp 1001-1720 | - - - | - - - | - - - |
| | C7 bp 101-510 | + + + | - - - | - - - |
| | C8 bp 1-405 | - - - | - - - | - - - |
| | C9 bp 101-405 | - - - | - - - | - - - |
| | C10 bp 1-300 | - - - | - - - | - - - |
| | C11 bp 101-300 | - - - | - - - | - - - |
| | C12 bp 226-510 | + + + | - - - | - - - |
| | C13 bp 326-510 | + + + | - - - | - - - |
| | C14 bp 456-510 | + | - - - | - - - |

Fig. 6

| | Fragment of CD83 intron 2 | Forward primer | Reverse primer |
|---|---|---|---|
|  | Fragment A 1239 bp | Intron2-A_for | Intron2-A_rev |
| 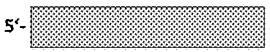 | Fragment B 2359 bp | Intron2-B_for | Intron2-B_rev |
|  | Fragment C 1-2220 bp | C-forward | C-reverse |
|  | Fragment C1 bp 1-1720 | C-forward | C-Kurz 3rev |
|  | Fragment C2 bp 1-1001 | C-forward | A-2 |
|  | Fragment C3 bp 1-525 | C-forward | A-1 |
|  | Fragment C4 bp 501-2220 | C-Kurz 1 | C-reverse |
| 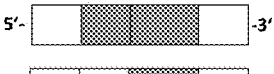 | Fragment C5 bp 501-1720 | C-Kurz 1 | C-Kurz 3rev |
|  | Fragment C6 bp 1010-1720 | C-Kurz 2 | C-Kurz 3rev |
| 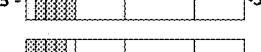 | Fragment C7 bp 101-510 | C-forward 2 | A-1b |
| 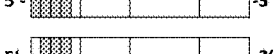 | Fragment C8 bp 1-405 | C-forward | A-4 |
|  | Fragment C9 bp 101-405 | C-forward 2 | A-4 |
| 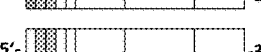 | Fragment C10 bp 1-300 | C-forward | A-3 |
| 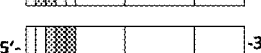 | Fragment C11 bp 101-300 | C-forward 2 | A-3 |
| 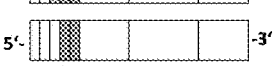 | Fragment C12 bp 226-510 | A-8 | A-1b |
|  | Fragment C13 bp 326-510 | A-9 | A-1b |
| 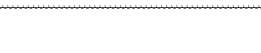 | Fragment C14 bp 456-510 | A-10 | A-1b |

FIG. 22

MUTANT CD83 PROMOTER AND USE THEREOF

This application is a 371 of International Patent Application No. PCT/EP2012/057760, filed Apr. 27, 2012, which claims foreign priority benefit under 35 U.S.C. §119 of European Patent Application No. 11164344.1, filed Apr. 29, 2011, the disclosures of which patent applications are incorporated herein by reference.

The present invention provides a mutant CD83 promoter comprising the promoter/enhancer regions of human CD83 and being dendritic cell-specific, and the use thereof, specifically for the treatment or prevention of diseases or medical conditions related to malignancy, autoimmunity or prevention of transplant rejections.

BACKGROUND OF INVENTION

The human CD83 gene is located on chromosome 6p23 and composed of five exons and four introns spanning over a total length of 19.284 kb (Berchtold, S. et al., Ann. Hum. Genet. 63:181-183 (1999)). Likewise, the murine CD83 gene spans over a total length of ~19 kb, consisting of five exons and four introns, although it is located on chromosome 13 band A 5. CD83 is expressed in most, if not all, vertebrate species. It has been reported to be expressed by humans, chimpanzee, horse, swine, cattle, panda, dog, rat, mouse, frog, elasmobranch and teleost fish, sharing the highest amino acids (aa) sequence homology with chimpanzee (*pan troglodytes*, 99%), horse, (*equus caballus*, 76%), cattle (*bos taurus*, 74%), swine (*sus scrofa*, 72%) and mouse (*mus musculus*, 65%) and to a lesser extend with fish (*oncorhynchus mykiss* and ginglymostoma cirratum, 28% and 32% respectively) (Lechmann, M. et al., Biochem. Biophys. Res. Commun. 329:132-139 (2005); Ohta, Y. et al. J. Immunol. 173:4553-4560 (2004)).

The human minimal CD83 promoter sequence was disclosed in Berchtold, S. et al. Immunobiology 205:231-246 (2002). A 3037 bp long fragment upstream of the transcription start codon has been cloned and used to narrow the core promoter sequence down to 261 bp. By bioinformatical analyses four specificity protein 1 (SP-1) and one NFκB-binding element were identified and could verified by electrophoretic mobility shift assays (EMSA). These findings are in concordance with those from other groups: McKinsey and colleagues described that NFκB regulates inducible CD83 gene expression in activated T lymphocytes (McKinsey, T. A. et al., Mol. Immunol. 37:783-788 (2000)) and Dudziak and co-workers published that Epstein Barr virus' latent membrane protein 1 (LMP1) induces CD83 expression in B cells via the NFκB-signalling pathway (Dudziak, D. et al., J. Virol. 77:8290-8298 (2003)). Interestingly, Berchtold and co-workers found similar activity of the 261 bp CD83 minimal promoter in several other cell types than DCs. This minimal promoter displayed activity in mature human moDCs, but also in the human monocyte cell line U937 as well as in human leukaemia Jurkat T cells (both expressing CD83) and in the murine DC-like cell line DC2.4.

The exact promoter sequence of the murine CD83 has not been identified yet, but consistent with the human CD83 promoter region, the murine 5' region of the CD83 gene lacks a clear TATA box sequence. However, no conservation of specific transcription factor binding sequences between mice and human were found yet in the minimal promoter region (Twist, C. J. et al., Immunogenetics 48:383-393 (1998)).

In summary, the human 261 bp CD83 minimal promoter showed neither cell type nor maturation specific activity for DCs. This leads to the conclusion that additional regulatory elements must be involved in the cell type- and stadium-specific regulation of the human CD83 gene expression, which have not been identified yet (Ilka Knippertz, I., Thesis Universität Erlangen-Nueremberg, 91-98. Jan. 7, 2008).

SHORT DESCRIPTION OF THE INVENTION

The full characterization of the human dendritic cell-specific CD83 promoter as well as the underlying molecular mechanisms of the cell type- and maturation status-specific CD83 regulation was now established. To identify regulatory elements contributing to the cell type specificity of the CD83 expression a ChIP-chip™ microarray directed against acetylated lysine 9 of Histone 3 (H3K9) in immature DCs (iDC), mature DCs (mDC) and human foreskin fibroblasts (HFF) was performed. The ChIP-assay revealed a region within CD83 intron 2 that was specifically H3K9 acetylated in mDCs, whereas iDCs and HFF cells did not show this type of acetylation. Deletion mutagenesis and luciferase reporter assays revealed a 185 bp long enhancer (185 bp enhancer) within this acetylated region that specifically induced the MP-261 in the DC-like cell line XS52 and mDCs, whereas the induction was absent in the control cell lines as well as in iDCs.

A biocomputational analysis of the MP-261 in combination with the 185 bp enhancer predicted three NFκB- and five SP1-sites in the MP-261 as well as two IRF-sites and one SP1-site in the 185 bp enhancer. Furthermore, a third regulatory element, the CD83 upstream promoter (UpP), was proposed. Two additional NFκB-, one IRF- and one SP1-site were predicted to lie within the UpP. Furthermore, the biocomputational model foretold the interaction of those three regulatory elements to form three copies of a well known NFκB-IRF-NFκB transcriptional module in trans. The formation of such a module in trans represents a completely new molecular mechanism that has not been described so far.

To prove this model, a series of experiments was performed. First, adenoviral transduction of luciferase reporter vectors proved in a chromosome-like configuration that all three regulatory elements, namely UpP, MP-261 and 185 bp enhancer have to be present in the same vector to induce transcription specifically in mature dendritic cells. This clearly proved the cooperation of all three regulatory elements to induce transcriptional activity in vitro.

Second, the function of predicted IRF- and NFκB-sites has been verified individually by loss of function and gain of function experiments, respectively: on the one hand mutation of the IRF-sites in the UpP and the enhancer revealed that all three sites are necessary for the induction of transcription in the tripartite complex in XS52 cells and mDCs. On the other hand cotransfection of p50, p65 and cRel in combination with IRF-5 verified the functionality of the NFκB-sites by inducing luciferase reporter plasmids containing the UpP and the MP-261 in 293T cells.

Taken together, the cell type- and maturation status-specific expression of CD83 has been proven to be regulated by a tripartite complex consisting of UpP, MP-261 and 185 bp enhancer. This complex forms specifically in mDCs and is mainly mediated through the interaction of IRF- and NFκB-transcription factors.

The invention thus provides the basis for a CD83 promoter that comprises the promoter/enhancer regions of human CD83 and is human dendritic cell-specific. This promoter is particularly suitable for the treatment or prevention of diseases or medical conditions related to malignancy, autoimmunity or prevention of transplant rejections.

In particular the invention provides:

(1) a CD83 promoter (hereinafter also referred to as "mutant CD83 promoter for distinguishing it from the wild-type CD83 promoter) comprising the CD83 Upstream promoter (UpP) sequence of SEQ ID NO:2, the CD83 Minimal Promoter (MP) sequence of SEQ ID NO:4 and the CD83 enhancer sequence of SEQ ID NO:5, or variants of said sequences having 90% homology over the entire length and/or being N- and/or C-terminally truncated by up to 30 nucleotides and having promoter activity, said UpP sequences being located upstream of said MP sequence and said enhancer sequence being located 200 to 4000 nucleotides upstream of the UpP sequence or 200 to 4000 nucleotides downstream of said MP sequence;

(2) a vector or viral vector comprising the mutant CD83 promoter of (1) above;

(3) a cell, tissue culture or transgenic non-human organism, which comprises the mutant CD83 promoter of (1) above, or the vector or viral vector of (2) above;

(4) the vector or viral vector of (2) above for use in (a) inducing anti-tumoral immune responses, (b) dampening unwanted immune responses in circumstances of autoimmune disorders, (c) dampening unwanted immune responses in circumstances of cell and/or organ transplantation, (d) inducing immune responses to viral and/or bacterial antigens in a patient in vivo;

(5) a pharmaceutical composition or vaccine comprising the vector or viral vector of (2) above;

(6) a method for producing dendritic cells ex vivo, said method comprises introducing a vector or viral vector of (2) above into a DC progenitor cell;

(7) a transfection reagent comprising the vector or viral vector of (2) above; and (8) a method for inducing anti-tumoral immune responses in a patient, dampening unwanted immune responses in circumstances of autoimmune disorders in a patient, dampening unwanted immune responses in circumstances of cell and/or organ transplantation in a patient, inducing immune responses to viral and/or bacterial antigens in a patient, or vaccinating a patient, said methods comprising administering the patient a suitable amount of the vector or viral vector of (2) above.

SHORT DESCRIPTION OF THE FIGURES

FIG. 1: CD83 is upregulated during DC maturation and is not expressed by HFF cells.

Figure 2:
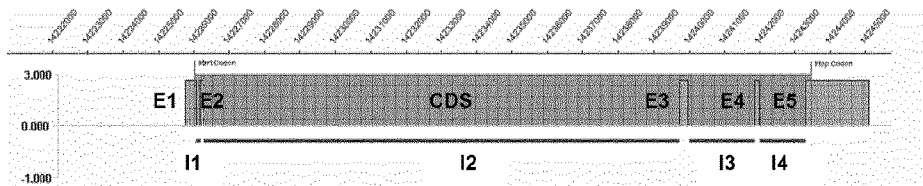
Figure 2:
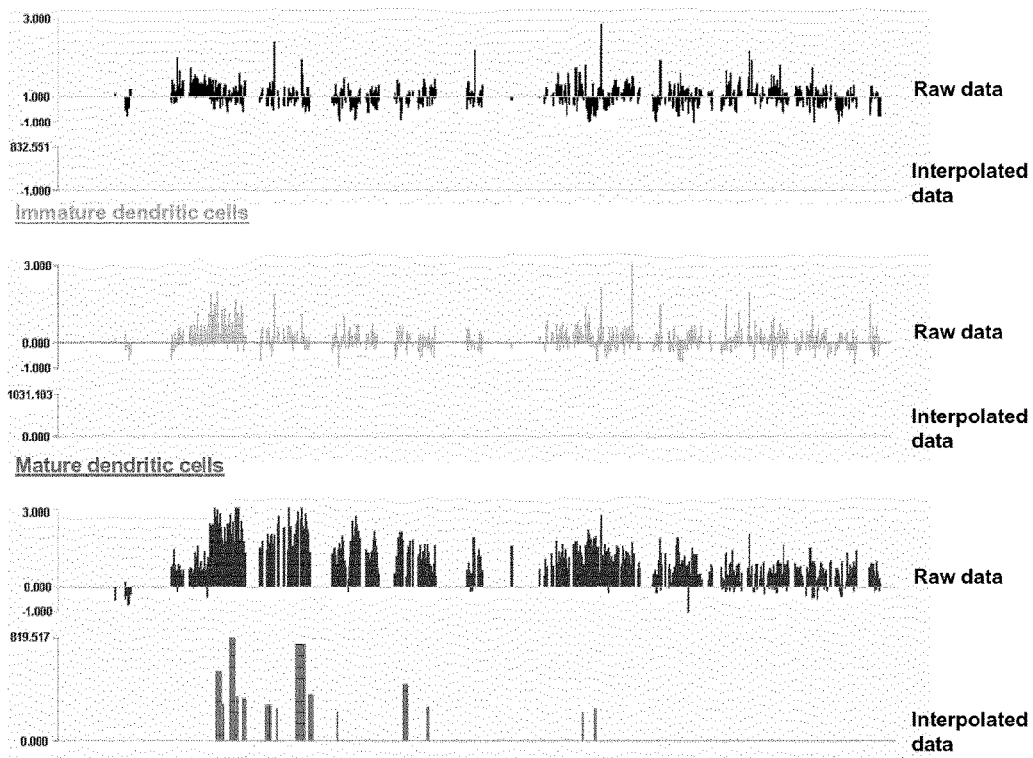
Figure 2:
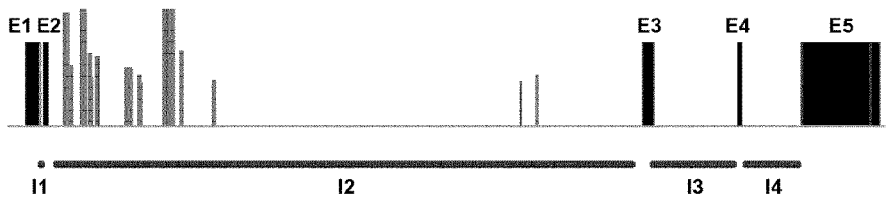

FIG. 2: Schematic depiction of the CD83 gene locus and the respective acetylation data resulting from the ChIP-chip™ microarray analysis.

Figure 3:
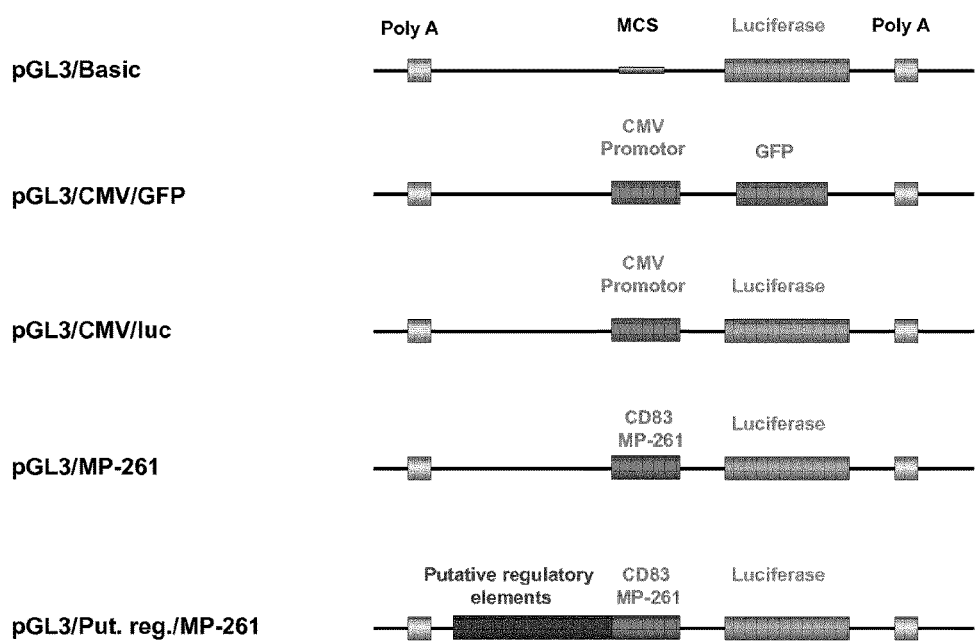

FIG. 3: Schematic depiction of constructs for gene reporter assays.

Figure 4:
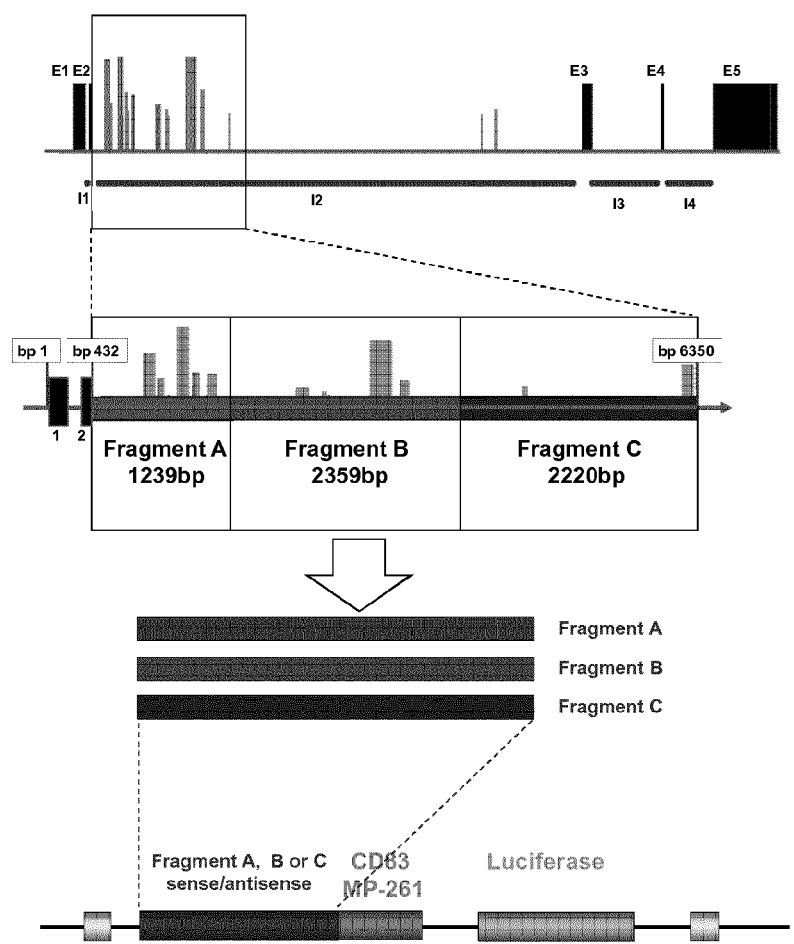

FIG. 4: Schematic depiction of the subcloning strategy of the hyper-acetylated region of CD83 intron 2.

Figure 5:
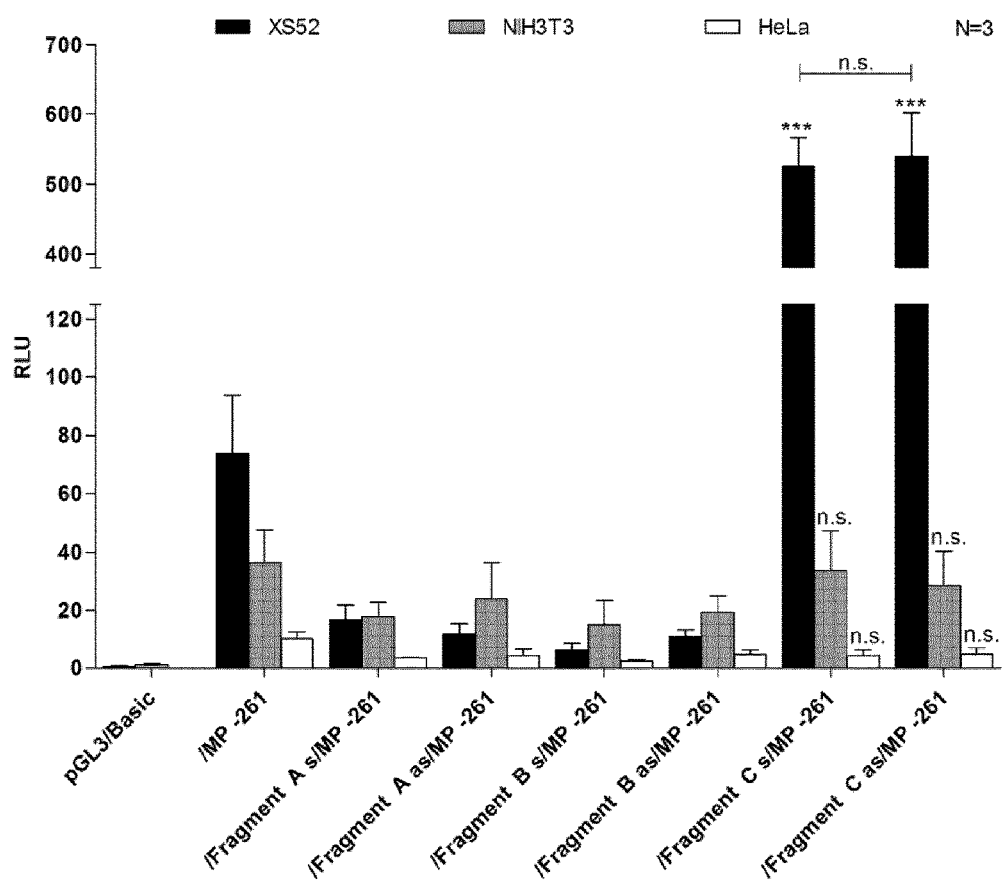

FIG. 5: Fragment C enhances the MP-261 activity specifically in XS52 cells.

FIG. 6: Schematic depiction of the deletion mutants C1-C14 of fragment C.

Figure 7:
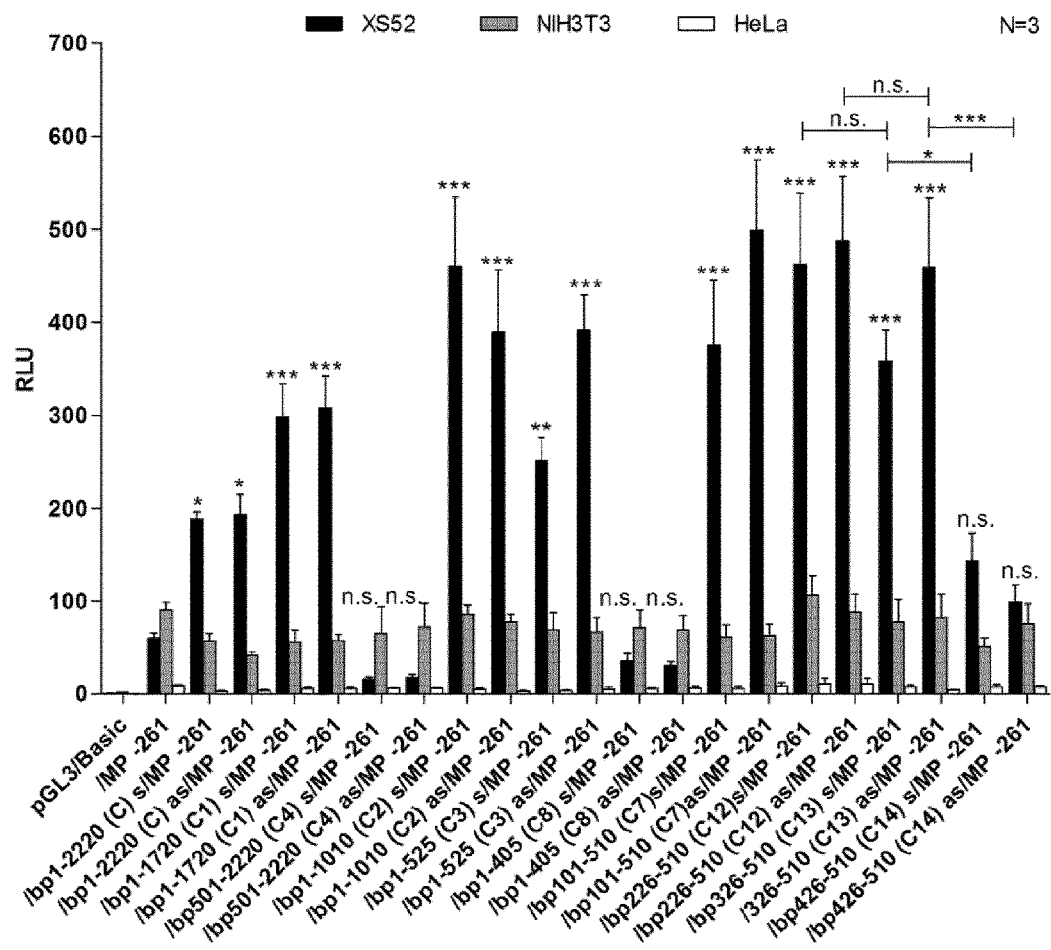

FIG. 7: The 185 bp long deletion mutant C13 of fragment C enhances the MP-261 activity specifically in XS52 cells.

Figure 8:
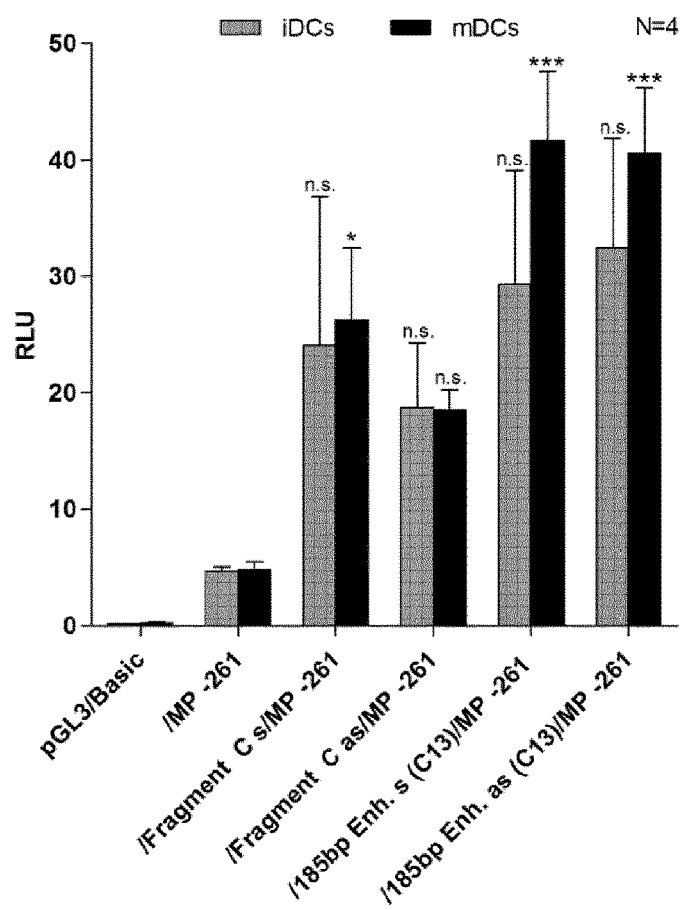

FIG. 8: Fragment C and the 185 bp enhancer induce the MP-261 activity specifically in mDCs.

Figure 9:
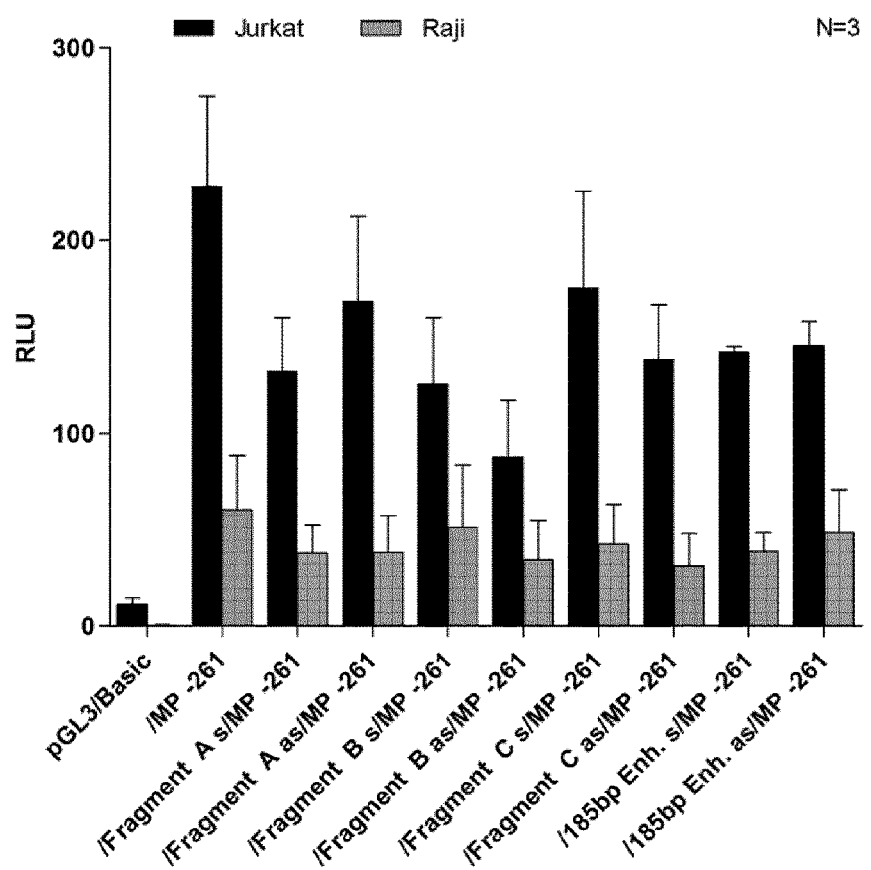

FIG. 9: Neither fragments A, B, C nor the 185 bp enhancer induce the MP-261 in Raji and Jurkat cells.

Figure 10:
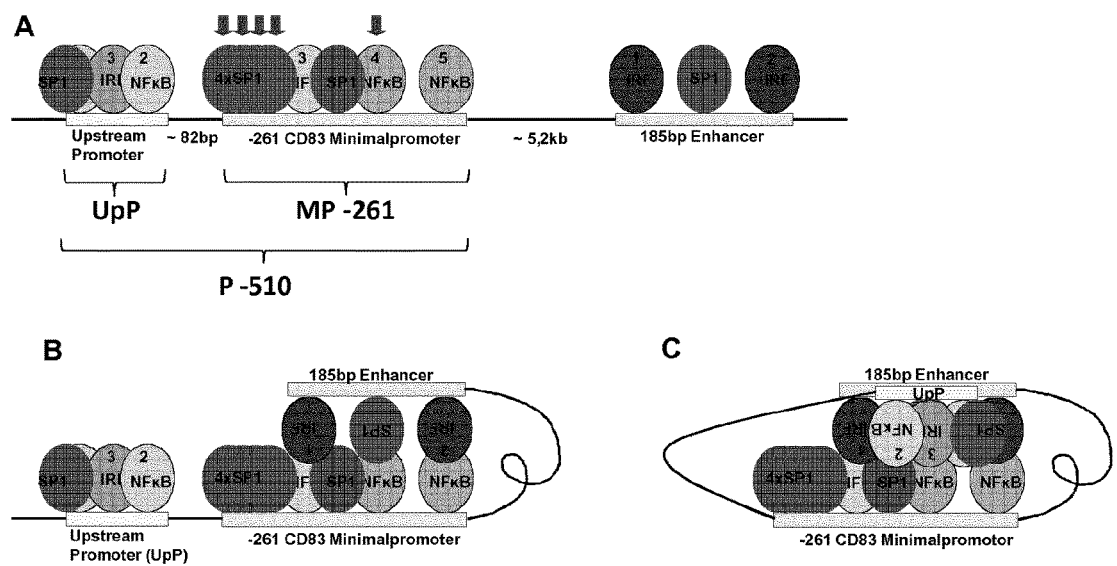

FIG. 10: Presumed bio-computational model for the interaction of the CD83 upstream promoter, the MP-261 and the 185 bp enhancer.

Figure 11:
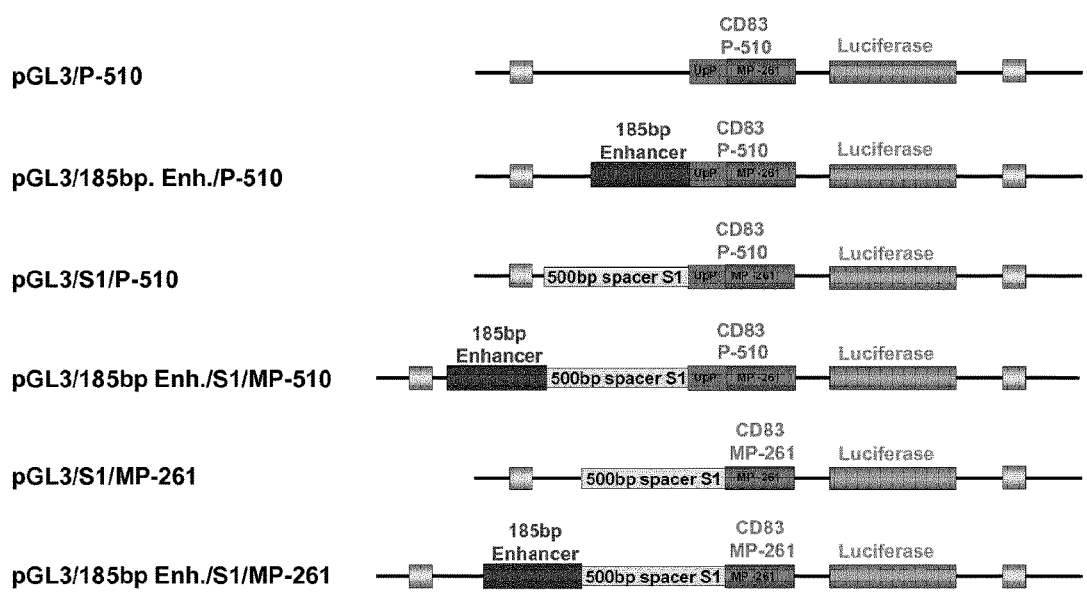

FIG. 11: Schematic depiction of reporter constructs containing the UpP and the spacer sequence S1.

Figure 12:
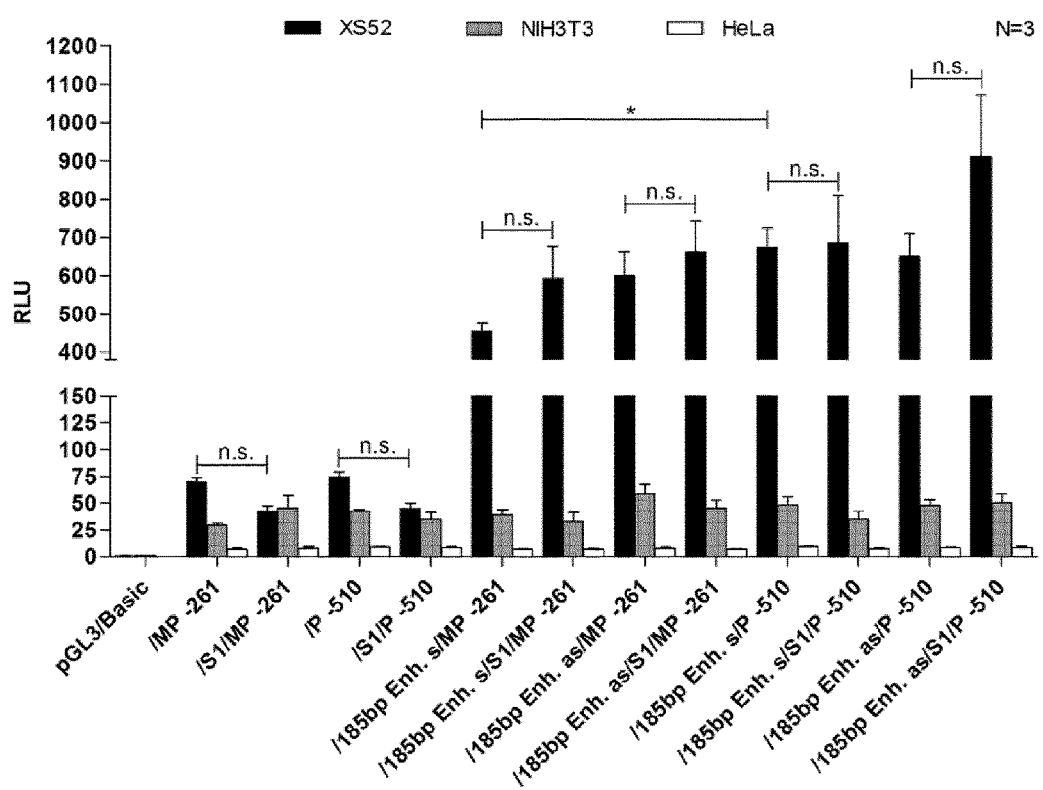

FIG. 12: The spacer sequence S1 does not significantly affect the induction of the MP-261 and the P-510 in XS52 cells.

Figure 13:
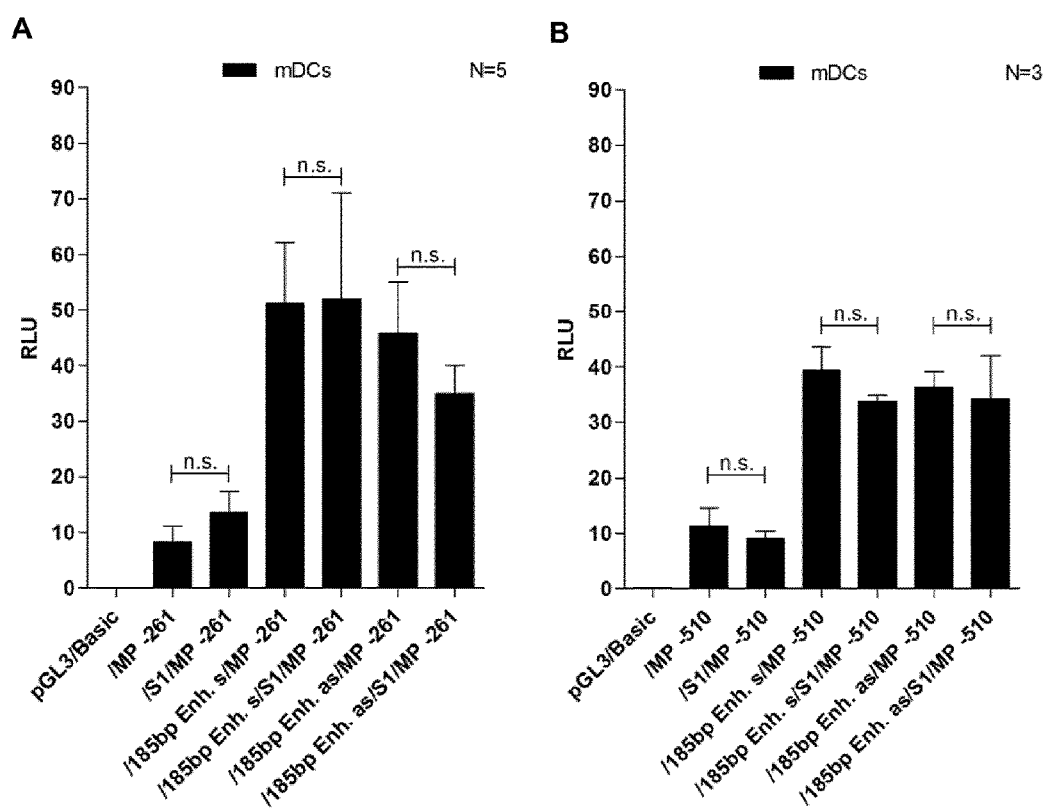

FIG. 13: (A) The spacer sequence S1 does not significantly affect the induction of the MP-261 in mDCs. (B) The spacer sequence S1 does not significantly affect the induction of the P-510 in mDCs.

Figure 14:
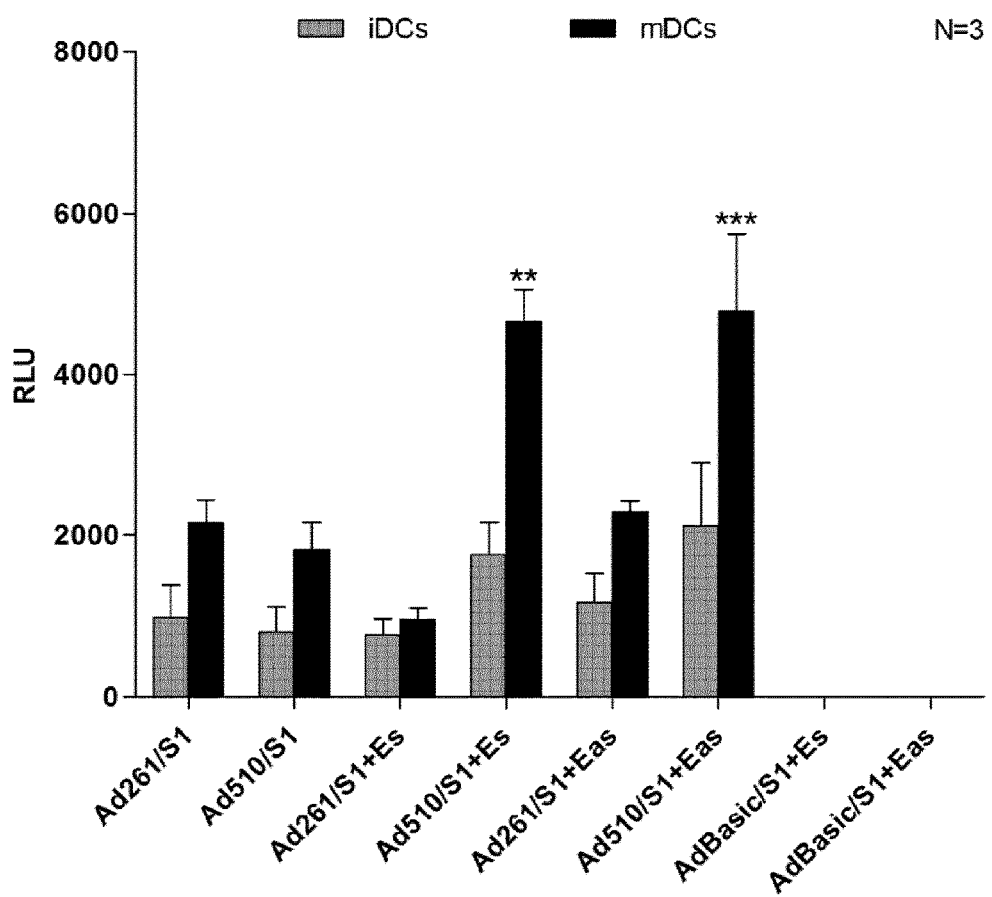

FIG. 14: (A) The ternary complex of UpP, MP-261 and 185 bp enhancer shows a specific transcriptional induction in mDCs.

Figure 15:
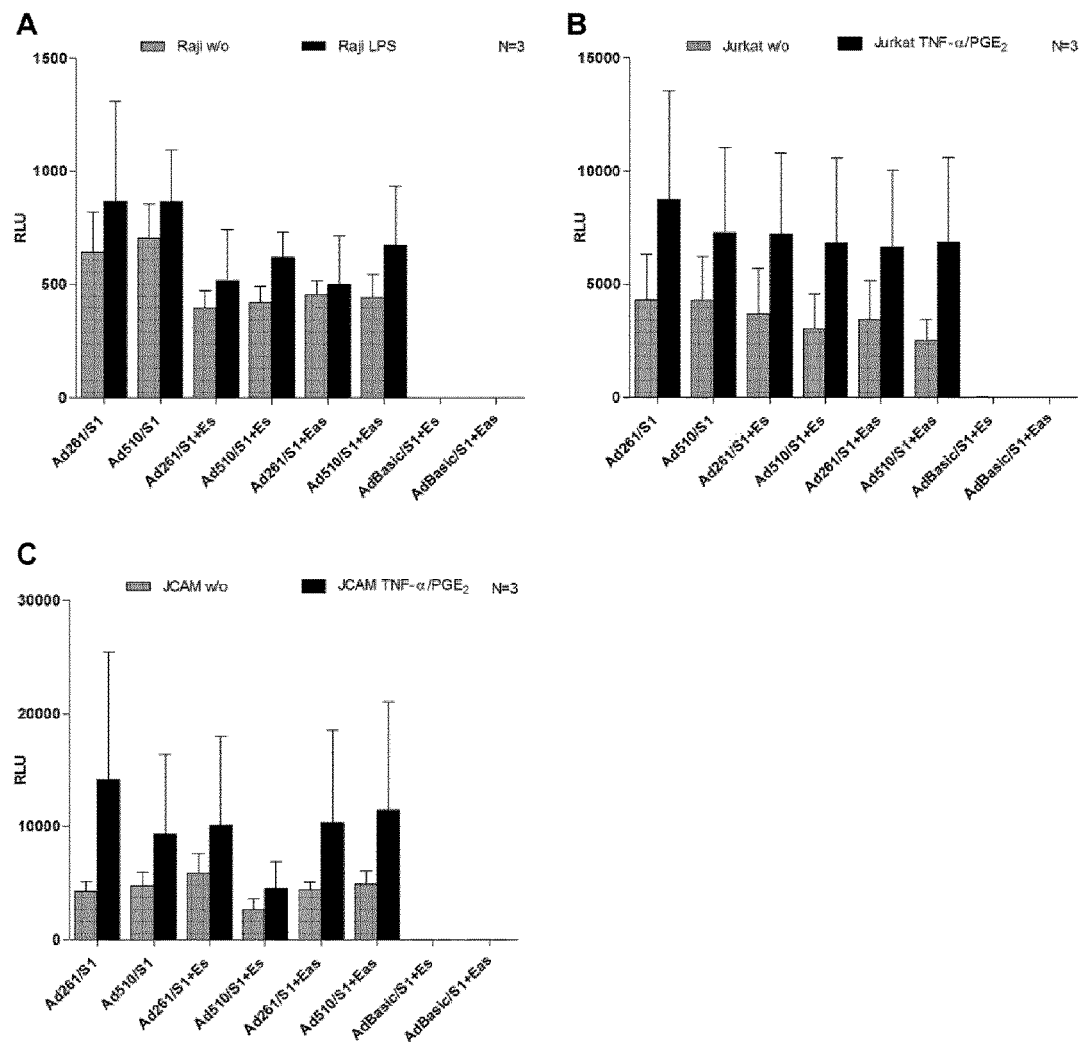

FIG. 15: (A)-(C) The ternary complex of UpP, MP-261 and 185 bp enhancer shows no specific transcriptional induction in Raji, Jurkat and JCAM cells.

Figure 16:
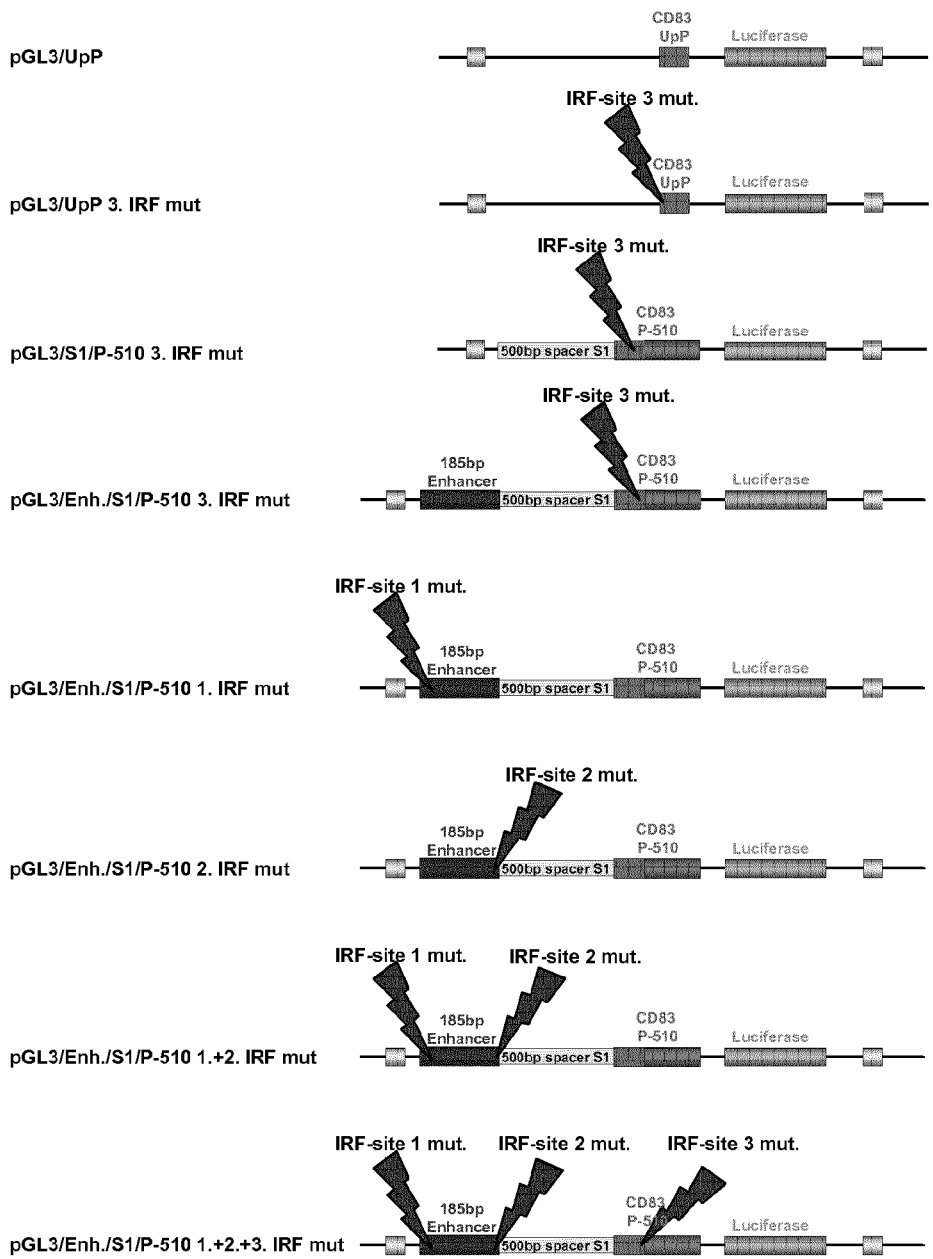

FIG. 16: Schematic depiction of reporter constructs containing mutated IRF-sites used for luciferase assays.

Figure 17:
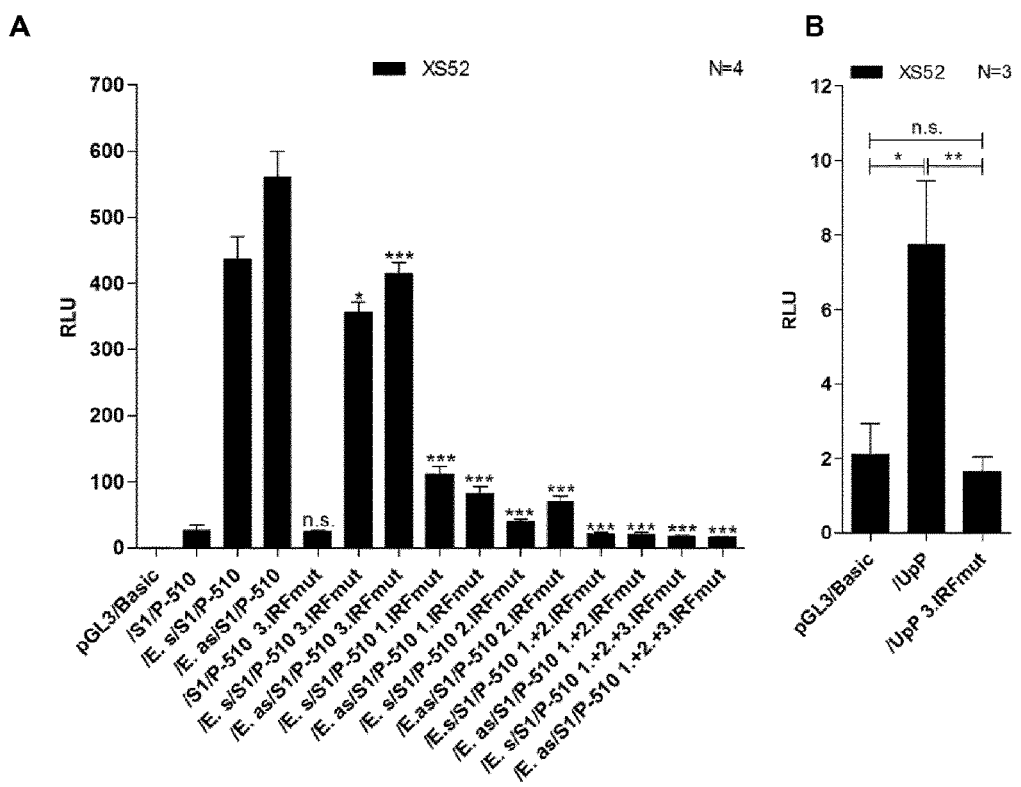

FIGS. 17: (A) and (B) Mutation of any of the three IRF-sites in the ternary complex significantly reduces the luciferase expression in XS52 cells.

Figure 18:
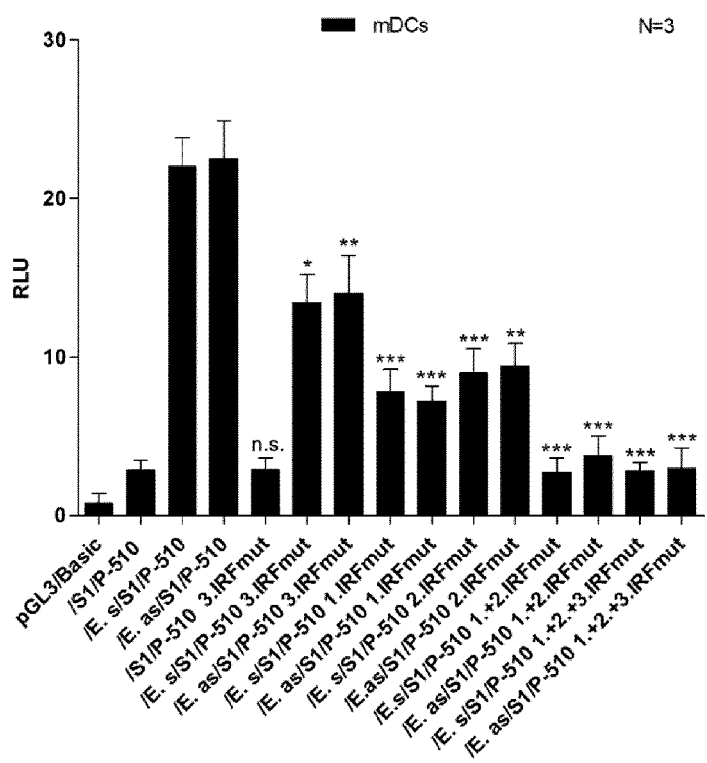

FIG. 18: Mutation of any of the three IRF-sites in the ternary complex significantly reduces the luciferase expression in mDCs.

Figure 19:
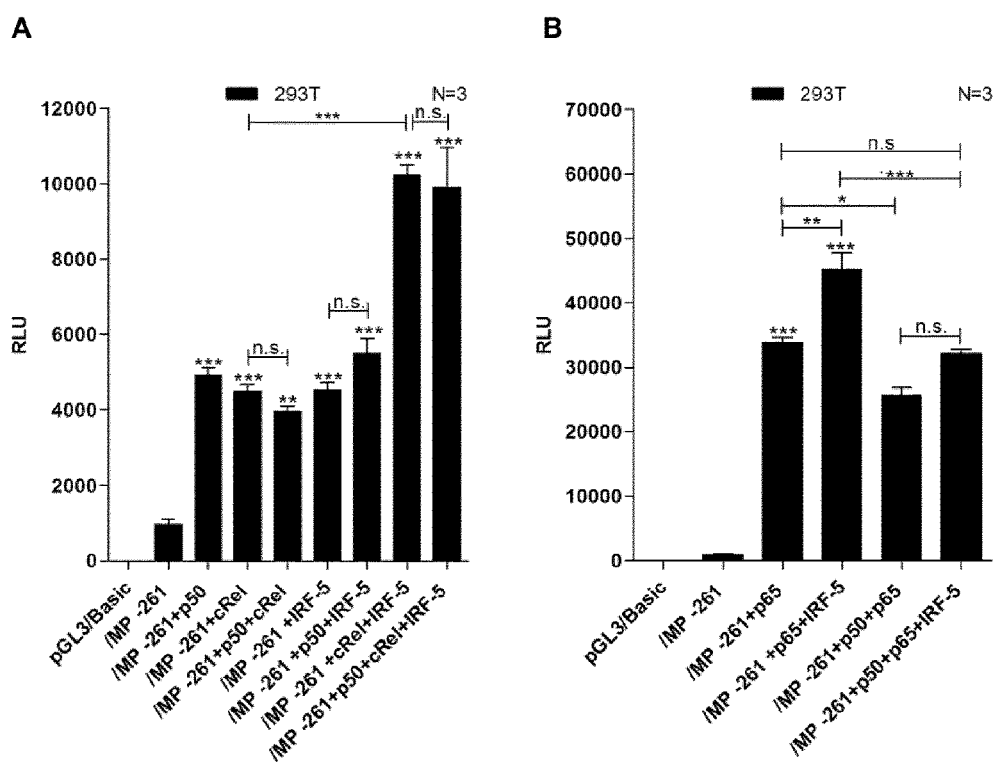

FIGS. 19: (A) and (B) Transcription factors of the NFκB-family and IRF-5 induce the MP-261 in 293T cells.

Figure 20:
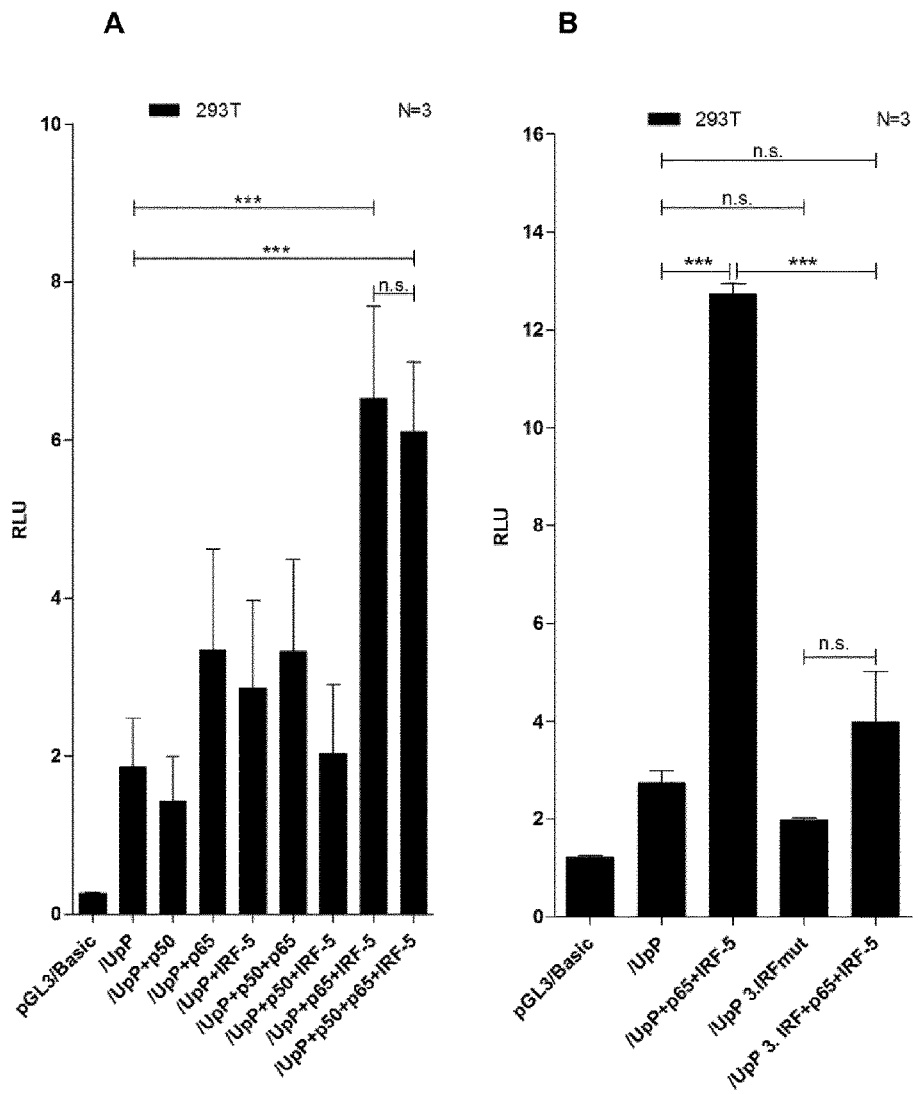

FIG. 20: (A) p65 and IRF-5 induce the UpP in 293T cells. (B) The induction of the UpP by p65 and IRF-5 is abrogated when the IRF-site 3 is mutated.

Figure 21:
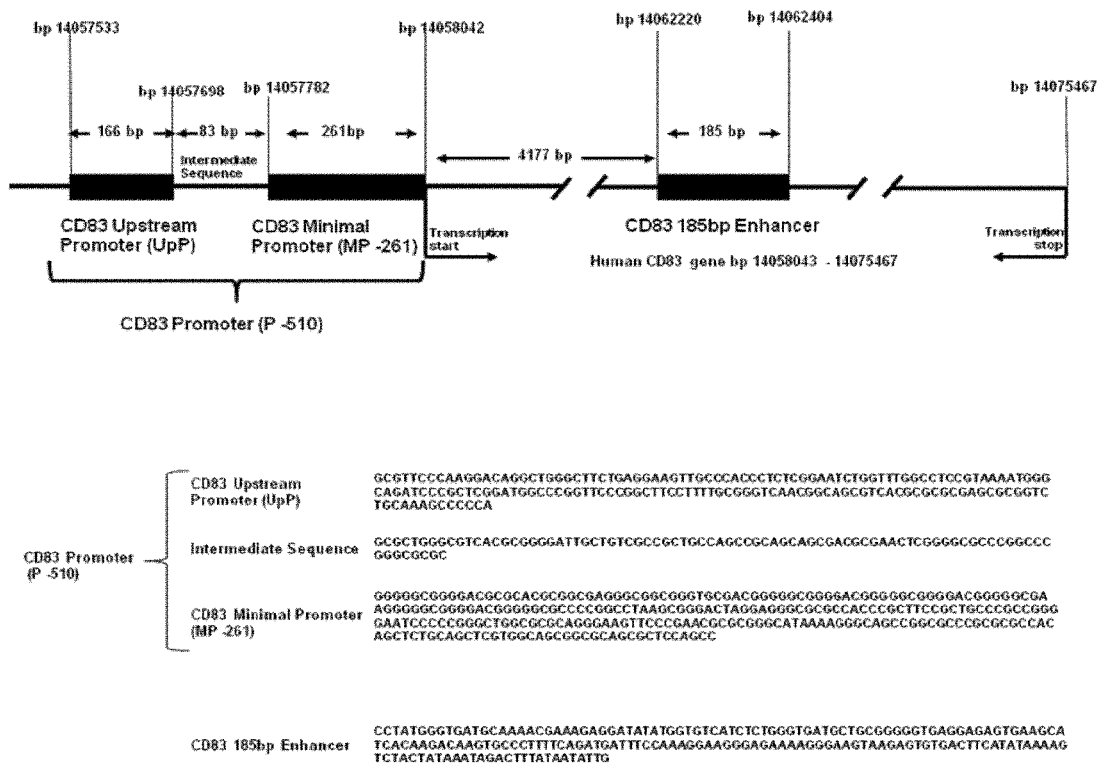

FIG. 21: Genomic sequences of the of functional human dendritic cell-specific CD83 promoter/enhancer regions CD83 Upstream promoter, Intermediate sequence, CD83 Minimal Promoter and 185 bp enhancer (NCBI genome build 37.2, contig GRCh37.p2). The 166 bp long CD83 upstream promoter (UpP) and the 261 bp long CD83 minimal promoter (MP-261) are separated by a 83 bp long intermediate sequence. Together these sequences constitute the CD83 promoter P-510. The P-510 cooperates with a 185 bp long enhancer element (185 bp enhancer) in the CD83 intron 2, located 4177 bp downstream of the CD83 transcription start. Referring to the NCBI human genome build 37.2, contig GRCh37.p2 (reference number NT_007592.15; SEQ ID NO:1), the UpP comprises the bp 14057533 to bp 14057698, the intermediate sequence bp 14057699 to Ser. No. 14/057,782, the MP-261 bp 14057783 to 14058042 and the 185 bp enhancer bp 14062220 to bp 14062404.

FIG. 22: Overview of luciferase reporter constructs and PCR primers used for cloning fragments of CD83 intron 2.

DETAILED DESCRIPTION OF THE INVENTION

The mutant CD83 promoter according to aspect (1) of the invention comprises the CD83 Upstream promoter (UpP) sequence of SEQ ID NO:2, the CD83 Minimal Promoter (MP) sequence of SEQ ID NO:4 and the CD83 enhancer sequence of SEQ ID NO:5, or variants of said sequences (i) having 90% homology over the entire length and having promoter activity and/or (ii) being N- and/or C-terminally truncated by up to 30 nucleotides and having promoter activity, said UpP sequences being located upstream of said MP sequence and said enhancer sequence being located 200 to 4000 nucleotides upstream of the UpP sequence or 200 to 4000 nucleotides downstream of said MP sequence.

The feature "having promoter activity" of the variants refers to the promoter activity of the starting mutant CD83 promoter.

The wording "being located upstream" and "being located upstream" according to the invention implies that the respective sequences are on the same nucleotide strand and are connected by linker/spacer nucleotide molecule (of a variable length, unless the length of the linker/spacer is specifically indicated.

According to the invention it is preferred that the distance between the UpP sequence and the MP sequence is 50 to 200 nucleotides, preferably 70 to 120 nucleotides. Also it is preferred that the distance between the UpP sequence/MP sequence and the enhancer is 200 to 4000 nucleotides, preferably 250 to 750 nucleotides.

According to the invention the variants of SEQ ID NOs: 2, 4 and 5 may have 90% homology, preferably 95% homology, most preferably 98% homology over the entire length of the respective basis sequence. Truncation by up to 30 nucleotides, or up to 20 nucleotides or up to 10 nucleotides are possible. Particularly preferred is that the UpP sequence has SEQ ID NO:2, the MP sequence has SEQ ID NO:4, and/or the CD83 enhancer sequence has SEQ ID NO:5.

Further preferred is that the UpP sequence is linked to the MP sequence by the intermediate sequence of SEQ ID NO:3 or a variant thereof having 95% homology to SEQ ID NO:3 over its entire length; and/or that the CD83 enhancer sequence is located 450 to 550 nucleotides upstream to the UpP sequence or 450 to 550 nucleotides downstream of the MP sequence, preferably 450 to 550 nucleotides upstream to the UpP sequence.

Particularly preferred mutant CD83 promoters comprises the sequence of nucleotides 29-1259 of SEQ ID NO:28 or the sequence of nucleotides 27-1257 of SEQ ID NO:29. Also preferred is that the mutant CD83 promoter is human dendritic cell-specific.

To fully characterize the CD83 promoter, including all regulatory elements that provide for the cell type and maturation status specificity of CD83 expression in mature DC, areas containing potential regulatory elements like e.g. enhancers were identified by the analysis of differential H3K9 acetylation in iDCs, mDCs and HFF cells using a ChIP-chip™ microarray assay. The first 6 kb of CD83 Intron 2 were revealed to be exclusively H3K9 acetylated in mDCs, hinting at a cell type and maturation status-specific hotspot of transcriptional activity in this area.

Next, the potential enhancer element within this area was narrowed down. This was achieved by mutation mutagenesis and luciferase assays. As a result, a 185 bp fragment (185 bp enhancer) of the H3K9 acetylated region within CD83 intron 2 has been shown to induce the CD83 minimal promoter (MP-261) in a cell type- and maturation status-specific manner in mDCs.

Next, the molecular mechanism underlying the induction of the MP-261 by the 185 bp enhancer was unraveled. Therefore, a biocomputational analysis was performed by the co-inventor Dr. Werner. The Analysis predicted three NFκB- and five SP1-binding sites in the MP-261, two IRF- and one SP1-site in the 185 bp enhancer and additionally two NFκB- and one IRF-site in a presumed upstream promoter (UpP). Furthermore, the formation of a tripartite regulatory complex, consisting of UpP, MP-261 and 185 bp enhancer was foretold. The formation of this complex was supposedly mediated by the interaction of the IRF- and NFκB-transcription factors, thereby forming three NFκB-IRF-NFκB transcriptional modules in trans.

To prove this model, the cooperation of all three predicted regulatory elements, namely UpP, MP-261 and 185 bp enhancer, as well as the functionality of the predicted NFκB- and IRF-sites had to be verified. Therefore, several different experimental approached were taken: (i) Adenoviral transduction with luciferase reporter vectors to prove the cooperation of the three regulatory elements in a chromosome-like configuration. (ii) Mutation of the three IRF-sites in the luciferase reporter plasmids to verify their functionality and significance for the formation of the tripartite regulatory complex. (iii) Induction of the predicted NFκB-sites by cotransfection of plasmids coding for members of the NFκB-transcription factor family and luciferase reporter plasmids to verify their functionality. Both the transcription factor binding sites as well as the cooperation of UpP, MP-261 and the 185 bp enhancer were thereby verified.

The invention is further described in the following Examples, which are not to be construed to limit the invention.

EXAMPLES

Methods
Transient Transfection Methods and Luciferase Reporter Assay
Transfection of DNA with the DEAE-Dextran Method:

For promoter analyses, adherent XS52, NIH3T3 and HeLa cells were transfected with reporter plasmid DNA containing the promoter construct and a gene for the firefly luciferase by the DEAE-Dextran method in triplicates. Hence, $2\times10^5$ cells per well were seeded in 12-well tissue culture plate (Falcon) and grown overnight at 37° C., 5% $CO_2$. The next day, 2.5 µg of endotoxin-free plasmid DNA were diluted in 150 µl of TBS buffer and mixed with 50 µl 5 mg/ml DEAE-Dextran solution reaching a volume of 200 µl per transfection. Subsequently 0.2 µl Chloroquine solution (1 µg/µl, Roth) were added to the reaction mix. Cells were washed 1× with 500 µl/well TBS buffer. Then, the DNA-DEAE-Dextran-solution was added and plates were incubated on a rocker for 30 min to 1 h at RT. Afterwards, the DNA-DEAE-Dextran-solution was replaced by 500 µl of 10% DMSO for 2 min, cells were washed with 2×2 ml warm DPBS and finally 2 ml per well of warm cell culture medium was added. Transfected cells were cultured for 2 days at 37° C. in a humidified atmosphere of 5% $CO_2$ before luciferase reporter assays were performed. Transfection efficiency was assessed by transfection of a GFP coding control plasmid and subsequent FACS analysis.

Electroporation of Rail and Jurkat Cell Lines:

For promoter analyses suspension Raji and Jurkat cells were transfected by electroporation with reporter plasmid DNA containing the promoter construct and a gene for the firefly luciferase.

Therefore, $10\times10^6$ cells were harvested, washed 1× in DPBS and resuspended in 250 µl fetal calf serum (PAA) containing 20 µg of DNA. The cell suspension was incubated 10 min at RT. Subsequently 250 µl of RPMI1640 without additives were added and cells were transferred to a 4 mm electroporation cuvette (Peqlab). Electroporation was performed with a Genepulser II (Bio-Rad) at 975 µF and 260 Volt. The cells were incubated for 3 min at RT and then transferred into 10 ml prewarmed growth medium and cultivated at 37° C., 5% $CO_2$. After 24 h 10 ml of growth medium were added. Cells were applied to a luciferase assay 48 h after electroporation. The electroporation efficiency was assessed by the electroporation of a GFP coding control plasmid and subsequent FACS analysis.

Lipofection of DNA with Lipofectamine™ LTX and PLUS™ (Invitrogen) Reagent:

For the generation and assembly of adenoviruses, 293 cells were transfected with Lipofectamine™ LTX without PLUS™ reagent in a T25 tissue culture flask (Nunc) as follows: For optimal transfection efficiency the cells were transfected at 40-60% confluence. On the day of transfection, 4 µg of PacI-digested pAd-plasmid in 20 µl water was mixed with 13 µl Lipofectamine™ reagent in 500 µl OptiMEM (Gibco) and incubated for 30 min at RT. The cells were washed 1× with DPBS and covered with 2.5 ml OptiMEM. After the incubation the transfection mix was added directly to the cells and incubated for 6 h at 37° C. in a humidified atmosphere of 5% $CO_2$. Afterwards the mixture was replaced by 7 ml of warm growth medium and cells were grown for 10-12 days until viral plaques could be detected. Viruses were then further amplified as described below.

For co-transfection of luciferase reporter constructs and pCDNA3.1 vectors coding for transcription factors, the Lipofectamine™ LTX with PLUS™ reagent was used. Therefore, $6 \times 10^4$ 293T cells per well were seeded in a 24-well tissue culture plate (Falcon) one day prior to transfection in 500 µl antibiotic free growth medium. On the day of transfection 0.5 µg of total DNA, consisting of 0.05 µg reporter construct, 0.15 µg for each transcription factor construct and pCDNA 3.1 vector backbone to fill up to 0.5 µg, were diluted in 100 µl OptiMEM (Gibco). Then 0.5 µl per transfection mix PLUS reagent were added to the transfection mix, mixed vigorously and incubated for 5 min at RT. Subsequently, 1.25 µl Lipofektamin™ LTX was added to the transfection mix, vortexed and incubated 30 min at RT. After incubation the whole reaction mix was added drop wise directly to the cells. Transfected cells were cultured for 2 days at 37° C. in a humidified atmosphere of 5% $CO_2$ before luciferase reporter assays were performed. Growth medium was changed after 24 h. The transfection efficiency was assessed by the lipofection of a GFP coding control plasmid and subsequent FACS analysis.

Electroporation of Dendritic Cells with DNA Using AMAXA Technology:

For further promoter analyses iDC were electroporated using the AMAXA Human Dendritic Cell Nucleofector Kit (Lonza) and the Nucleofector I electroporation device (Lonza), according to the manufacturer's instructions. In brief: After harvesting and washing with warm DPBS, $2 \times 10^6$ immature DCs were resuspended in 100 µl freshly prepared electroporation solution (provided with the Nucleofector Kit) containing 4 µg of plasmid DNA. Cells were transferred to the electroporation cuvette and electroporated with program U-2. Immediately after electroporation 500 µl of RPMI1640 without additives were added to the cuvette and the whole cell suspension was transferred in 12-well tissue culture plate (Falcon) containing 600 µl of prewarmed RPMI1640 supplemented with 2% autologous serum, 500 U/ml human recombinant IL-4 and 800 U/ml human recombinant GM-CSF (both CellGenix). Directly after the transfer, the cell suspension was divided into 2 wells by pipetting 600 µl in an empty well. After 4 h 1.4 ml RPMI1640 supplemented with 1% autologous serum, 250 U/ml IL-4, 400 U/ml GM-CSF and, for cells to be matured, with LPS to a final concentration of 0.1 ng/ml, was added to the cells, which were cultured 24 h at 37° C. in a humidified atmosphere of 5% $CO_2$ before luciferase reporter assays were performed. The electroporation efficiency, generation and maturation of the dendritic cells were assessed by the electroporation of a GFP coding control plasmid and antibody staining of the appropriate lineage and maturation markers, respectively, by subsequent FACS analysis.

Luciferase Reporter Assay:

Measurements of luciferase activity of DNA-transfected or adenovirally transduced cell lines and moDCs were performed in triplicates with the Luciferase Assay System (Promega) 1-2 days after transfection. Adherent 293T, HeLa, XS52 and NIH3T3 cells were washed with warm DPBS and then 200 µl/well 1× Luciferase Cell Culture Lysis Reagent (Promega, diluted 1:5 with distilled water) were added before plates were frozen for at least 2 h to −80° C. Raji, Jurkat, JCAM and dendritic cells were first transferred to a reaction vial and then washed in 1 ml warm DPBS. Afterwards cells were collected by centrifugation (500 g, 5 min, RT) and lysed with 200 µl/vial 1× Luciferase Cell Culture Lysis Reagent and frozen to −80° C. for at least 2 h. Subsequently, plates or vials were thawed at RT and 10 µl (293T cells) or 20 µl (DC, Raji and Jurkat, JCAM) of cell lysate were mixed with 50 µl of Luciferase Assay Substrate (Promega) in a 96-well LumiNunc plate (Nunc). Determination of RLUs (relative luminescence units) was performed in a Wallac fluorometer (Perkin-Elmer, Rotgau) and normalized to the protein concentration of the lysate.

Recombinant Adenoviruses

Cloning of Plasmids Containing the Recombinant Adenoviral Genome:

For the generation of plasmids containing the recombinant adenoviral genome the pAdEasy1-system was used. Resulting plasmids were transfected into 293 cells for virus assembly and amplification.

Preparation of Recombinant Adenoviruses:

All viruses were amplified in 293 cells and purified by two rounds of CsCl equilibrium density gradient ultracentrifugation. Therefore, transfected 293 cells which show viral plaques were harvested, centrifuged at 1100 rpm for 5 min at 4° C. and then resuspended in 5 ml RPMI1640/2% FCS. Virus was released from cells by 3 freeze-thaw cycles and cell debris was removed by centrifugation of the lysate at 4000 rpm for 15 min at 4° C. Supernatant (2 ml) containing the virus was used to infect new 293 cells in increasing numbers (up to 15×T175 flasks) to amplify the virus; the remaining supernatant was stored at −80° C. for further rounds of virus production. Viruses from 15×T175 flasks of 293 cells were prepared by 3 freeze-thaw cycles as described above and then loaded onto a CsCl gradient. For the CsCl equilibrium density gradient, 3 ml of CsCl at a density of 1.41 g/ml was overlaid with 5 ml of CsCl at a density of 1.27 g/ml and then the supernatant containing the enriched virus was filled up to 7 ml with DPBS and loaded onto the gradient. After ultracentrifugation at 32000 rpm for 2 h at 4° C., the virus band was harvested, diluted in HEPES buffer to 8 ml and loaded onto a second CsCl equilibrium density gradient as described above. Viruses were spun in an ultracentrifuge at 32000 rpm for 24 h at 4° C., before harvesting and purification with a PD-10 tip (GE Healthcare) according to the manufacturer's instructions. Finally, eluted virus (in DPBS) was mixed with 10% Glycerin and aliquots of 25 µl were frozen to −80° C. Verification of viral genomes and exclusion of wild-type contamination was performed by PCR. Physical particle concentration [viral particles (vp)/ml] was determined by $OD_{260}$ reading and infectious particle concentration was determined by $TCID_{50}$ assay on 293 cells.

Determination of the Physical Particle Concentration:

The physical particle concentration is defined by the amount of virus particles per ml [vp/ml]. To quantify the viral DNA, the virus preparation was diluted at different ratios (1:3, 1:5, 1:10, 1:50, 1:100) with viral lysis buffer (VLB [10 mM TE, 0.5% SDS]) and incubated at 56° C. in a thermomixer (Eppendorf) for 10 min. Cooled samples were measured with a spectrophotometer (Eppendorf) at $OD_{260}$ and the mean value was calculated considering the dilution factors.

Determination of the Infectious Particle Concentration:

The concentration of infectious virus particles is determined by the "tissue culture infectious dose 50" ($TCID_{50}$)-method. Therefore, 293 cells were seeded in a 96-well tissue culture plate (Falcon) at a density of $10^5$/well in RPMI1640/2% FCS. The virus was diluted from $10^{-1}$ to $10^{-12}$ in RPMI1640/2% FCS and cells were infected with two dilution series each. Cells were incubated at 37° C., 5% $CO_2$ and 10 as well as 12 days after infection cell lysis was assessed microscopically. Wells that showed at least one plaque were considered "positive".

Adenoviral Transduction of Cells:

Immature day 5 DCs were seeded in 12-well tissue culture plates (Falcon) at a concentration of $1 \times 10^6$ cells/well in 250 µl medium supplemented with 800 U/ml GM-CSF and 500 U/ml IL-4. Immediately, adenovirus at 500 $TCID_{50}$/cell in a final volume of 250 µl medium without cytokines was added to the cells. After 1.5 h of incubation at RT, 2.5 ml of growth medium replenished with cytokines as described before was added per well. If mDCs were needed, LPS was added 4 h after transduction to final concentration of 0.1 ng/ml.

Raji, Jurkat and JCAM cells were seeded in 12-well tissue culture plates (Falcon) at a concentration of $1 \times 10^6$ cells/well in 250 µl RPMI1640 medium supplemented with 2% FCS. Immediately, adenovirus at 500 $TCID_{50}$/cell (Jurkat and JCAM cells) or 50 $TCID_{50}$/cell (Raji) in a final volume of 250 µl RPMI1640 medium supplemented with 2% FCS was added to the cells. After 1.5 h of incubation at RT on the rocker, 2.5 ml of growth medium replenished with 10% FCS were added per well. To determine transduction efficacy, cells were transduced with Ad5TL and the percentage of living green fluorescent cells was assessed by flow cytometric analysis with a "FACScan" flowcytometer (BD Biosciences, Heidelberg). Only experiments that yielded transduction efficiencies of more than 70% were evaluated and are shown.

Polymerase Chain Reaction (PCR):

PCR was used to (i) amplify DNA fragments for cloning from either chromosomal- or plasmid DNA and (ii) to screen adenoviral DNA for insertions.

(i) DNA fragments amplified for cloning were generated in a final reaction volume of 50 µl using a DNA polymerase containing proof-reading activity (Platinum Pfx DNA Polymerase, Invitrogen) according to the manufacturer's instructions.

(ii) PCR reactions for screening of adenoviral DNA were performed in a final reaction volume of 25 µl with a recombinant Taq DNA Polymerase from Invitrogen according to the manufacturer's instructions.

TABLE 1

PCR program for amplification of DNA fragments

| Step | Temperature | Time | Cycles |
|---|---|---|---|
| Initial denaturation | 95° C. | 5 min | 1x |
| Denaturation | 95° C. | 1 min | 25x |
| Annealing | 56° C.-62° C. | 1 min | to |
| Extension | 68° C. | 0.5 min-2 min | 30x |
| Final extension | 68° C. | 10 min | 1x |
| Pause | 4° C. | ∞ | |

Materials

Schematic Depiction of CD83 Intron 2 Fragments for Luciferase Assay:

Intron 2 was divided into 3 fragments (A, B, C) and subcloned in the pGL3/MP-261 reporter construct. Subsequently fragment C was narrowed down via deletion mutagenesis in the fragments C1-C14.

FIG. 22 provides an overview of luciferase reporter constructs and PCR primers used for cloning fragments of CD83 intron 2.

Adenoviruses

TABLE 3

Adenoviruses

| Adenovirus | Specification |
|---|---|
| Ad5TL | Replication deficient adenovirus serotype 5; E1 region replaced by a CMV-GFP cassette Kindly provided by D.T. Curiel, Birmingham, AL, USA |
| Ad5Luc1 | Replication deficient adenovirus serotype 5; E1 region replaced by a CMV-luciferase cassette Kindly provided by D.T. Curiel, Birmingham, AL, USA |
| Ad261/S1 | Replication deficient adenovirus serotype 5; E1 region replaced by a MP −261/S1-luciferase cassette |
| Ad510/S1 | Replication deficient adenovirus serotype 5; E1 region replaced by a P −510/S1-luciferase cassette |
| Ad261/S1 + Es | Replication deficient adenovirus serotype 5; E1 region replaced by a MP −261/S1/185 bp enhancer sense-luciferase cassette |
| Ad261/S1 + Eas | Replication deficient adenovirus serotype 5; E1 region replaced by a MP −261/S1/185 bp enhancer antisense-luciferase cassette |
| Ad510/S1 + Es | Replication deficient adenovirus serotype 5; E1 region replaced by a P −510/S1/185 bp enhancer sense-luciferase cassette |
| Ad510/S1 + Eas | Replication deficient adenovirus serotype 5; E1 region replaced by a P −510/S1/185 bp enhancer antisense-luciferase cassette |
| AdBasic/S1 + Es | Replication deficient adenovirus serotype 5; E1 region replaced by a 185 bp enhancer sense-luciferase cassette |
| AdBasic/S1 + Eas | Replication deficient adenovirus serotype 5; E1 region replaced by a 185 bp enhancer sense-luciferase cassette |

Cell Lines and Cell Culture Media:

If not indicated otherwise, all cell culture media and reagents were purchased by Lonza (Basel, Switzerland) and PAA (Cölbe).

TABLE 4

Cell lines and cell culture media

| Cell type | Short definition | Culture medium |
|---|---|---|
| 293(T) | Human embryonic kidney cell line, transformed with sheared adenovirus genome (stably transfected with large T antigen) | Dulbecco's Modified Eagle Medium (DMEM) (Lonza) without L-Glutamine, 4.5 g glucose/l (Lonza), 10% FCS (PAA), 1% Penicillin/Streptomycin/L-Glutamine (PAA) |
| HeLa | Human cervix carcinoma cell line | Dulbecco's Modified Eagle Medium (DMEM) (Lonza) without L-Glutamine, 4.5 g glucose/l (Lonza) 10% FCS (PAA)1% Penicillin/Streptomycin/L-Glutamine (PAA) |
| HFF | Human foreskin fibroblast primary cells | Minimum Essential Medium (DMEM) (Lonza) without L-Glutamine (Gibco), 7.5% FCS (PAA), 1% L-Glutamine (PAA), 0.001% Gentamycin |
| Jurkat | T cell leukemia derived T lymphocyte cell line | RPMI1640 without L-Glutamine (Lonza), 10% FCS (PAA), 1% Penicillin/Streptomycin/L-Glutamine (PAA) |
| NIH3T3 | BALB/c derived embryonic fibroblast cell line | Dulbecco's Modified Eagle Medium (DMEM) (Lonza) without L-Glutamine, 4.5 g glucose/l (Lonza), 10% FCS (PAA), 1% Penicillin/Streptomycin/L-Glutamine (PAA) |
| NS47 | BALB/c derived fibroblast cell line | Iscove's Modified Dulbecco's Medium (IMDM) (Lonza) without L-Glutamine (Lonza), 10% FCS (PAA), 1% Penicillin/Streptomycin/L-Glutamine (PAA), 1% Sodium pyruvate (PAA) |
| PBMC | (Human) Peripher blood mononuclear cells | RPMI1640 without L-Glutamine (Lonza), 1% human autologous serum, 1% Penicillin/Streptomycin/L-Glutamine (PAA), 1% Hepes (Lonza) |
| Raji | Burkitt's lymphoma derived lymphoblastoid B cell line | RPMI1640 without L-Glutamine (Lonza), 10% FCS (PAA), 1% Penicillin/Streptomycin/L-Glutamine (PAA), 1% Hepes (Lonza) |
| XS52 | BALB/c derived DC-like cell line | Iscove's Modified Dulbecco's Medium (IMDM) (Lonza) without L-Glutamine (Lonza), 10% FCS (PAA), 1% Penicillin/Streptomycin/L-Glutamine (PAA), 1% Sodium pyruvate (PAA), 10% Supplement NS47, 10 ng/ml murine GM-CSF |
| JCAM | T cell leukemia derived T lymphocyte cell line, similar to Jurkat, but lacking the LCK kinase | RPMI1640 without L-Glutamine (Lonza), 10% FCS (PAA), 1% Penicillin/Streptomycin/L-Glutamine (PAA) |

DNA Modifying Enzymes

TABLE 5

DNA modifying enzymes

| Enzyme | Supplier |
|---|---|
| DNA restriction enzymes | New England Biolabs (NEB [Frankfurt/Main]) |
| Alkaline Phosphatase, Calf Intestinal (CIP) | New England Biolabs (NEB [Frankfurt/Main]) |
| T4 DNA ligase (Rapid ligation kit) | Roche (Mannheim) |
| Platinum Pfx polymerase | Invitrogen (Karlsruhe) |
| T4 Poly nucleotide kinase (T4-PNK) | New England Biolabs (NEB [Frankfurt/Main]) |
| Klenow fragment of DNA Polymerase I | New England Biolabs (NEB [Frankfurt/Main]) |

Human Cytokines and Maturation Agents

TABLE 6

Human cytokines and maturation agents

| Cytokine/Agent | Stock concentration | Purity | Company |
|---|---|---|---|
| Lipopolysaccharide (LPS) | 1 mg/ml | | Sigma-Aldrich, München |
| Recombinant GM-CSF | $4 \times 10^4$ U/ml | >95% | Cell Genix, Freiburg |
| Recombinant IL-4 | $2 \times 10^5$ U ml | >95% | Cell Genix, Freiburg |
| Recombinant IL-6 | $1 \times 10^6$ U/ml | >95% | Cell Genix, Freiburg |

Cloning

Luciferase Reporter Constructs

Notes and Abbreviations:

s: sense; as: antisense; CDS: coding sequence; enh: enhancer; UPP: upstream promoter; S1: spacer sequence 1.

TABLE 7

Cloned luciferase reporter constructs

| Donor/template | Excision method | Insert | Recipient | Result |
|---|---|---|---|---|
| pEGFP-N1 | Restriction digest; HindIII/XbaI | GFP CDS | pGL3/CMV_luc; HindIII/XbaI (luc CDS replaced) | pGL3/CMV_GFP |
| RP1-258E1 | PCR; KpnI | CD83 intron 2 fragment A | pGL3/MP-261; KpnI | pGL3/fragment A s_as/MP-261 |
| RP1-258E1 | PCR; KpnI | CD83 intron 2 fragment B | pGL3/MP-261; KpnI | pGL3/fragment B s_as/MP-261 |
| CMVβL/cRel | Restriction digest; HindIII/XbaI | cRel CDS | pCDNA 3.1; HindIII/XbaI | pCDNA 3.1/cRel |
| CMVβL/p50 | Restriction digest; HindIII/XbaI | p50 CDS | pCDNA 3.1; HindIII/XbaI | pCDNA 3.1/p50 |
| CMVβL/p65 | PCR; HindIII/XbaI | P65 CDS | pCDNA 3.1; HindIII/XbaI | pCDNA 3.1/p65 |
| pGL3/185bp enh. s/MP-261 | Restriction digest; KpnI | 185 bp enhancer | pGL3/Basic; KpnI | pGL3/185bp enh. s_as |
| pGL3/fragment C/MP-261 | PCR; KpnI | 185 bp enhancer | pGL3/MP-261; KpnI | pGL3/185bp enh s_as/MP-261 |
| Geneart standard vector/CD83_-510 | Restriction digest; NheI/SmaI (blunt) | UPP | pGL3/Basic; NheI/XhoI (blunt) | pGL3/UPP |
| Geneart standard vector/CD83_-510 | Restriction digest; NheI/SmaI (blunt) | UPP | pGL3/185bp enh. s_as/MP-261; NheI/XhoI (blunt) | pGL3/185bp enh. s_as/UPP |
| RP3-380E11 | PCR; SacI/MluI | S1 | pGL3/UPP SacI/MluI | pGL3/UPP + S1 |
| RP3-380E11 | PCR; SacI/MluI | S1 | pGL3/185bp enh. s_as/UPP SacI/MluI | pGL3/185bp enh. s_as/UPP + S1 |
| Geneart standard vector/CD83_-510 | Restriction digest; NheI/XhoI | P-510 | pGL3/MP-261 NheI/XhoI | pGL3/P-510 |
| Geneart standard vector/CD83_-510 | Restriction digest; NheI/XhoI | P-510 | pGL3/185bp enh s_as/MP-261 NheI/XhoI | pGL3/185bp enh. s_as/P-510 |
| RP3-380E11 | PCR; SacI/MluI | S1 | pGL3/P-510; SacI/MluI | pGL3/P-510 + S1 |
| RP3-380E11 | PCR; SacI/MluI | S1 | pGL3/185bp enh. s_as/P-510; SacI/MluI | pGL3/185bp enh. s_as/P-510 + S1 |
| RP3-380E11 | PCR; SacI/MluI | S1 | pGL3/MP-261; SacI/MluI | pGL3/MP-261 + S1 |
| RP3-380E11 | PCR; SacI/MluI | S1 | pGL3/185bp enh s_as/MP-261; SacI/MluI | pGL3/185bp enh s_as/MP-261 + S1 |
| RP3-380E11 | PCR; KpnI | CD83 intron 2 fragment C | pGL3/MP-261; KpnI | pGL3/fragment C s_as/MP-261 |
| RP3-380E11 | PCR; KpnI | CD83 intron 2 fragment A | pGL3/MP-261; KpnI | pGL3/fragment A s_as/MP-261 |
| RP3-380E11 | PCR; KpnI | CD83 intron 2 fragment B | pGL3/MP-261; KpnI | pGL3/fragment B s_as/MP-261 |
| pGL3/fragment C/MP-261 | PCR; KpnI | CD83 intron 2 fragments C1-C14 | pGL3/MP-261; KpnI | pGL3/fragment C1-C14 s_as/MP-261 |

Luciferase Reporter Constructs with Mutated IRF-Sites

Notes and Abbreviations:

Via PCR mutagenesis the IRF-Sites 1 and 2 in the 185 bp enhancer were mutated by PCR mutagenesis. The 3$^{rd}$ IRF-site in the P-510 promoter (or rather in the UpP) was mutated by GENEART and provided in the "GENEART standard vector/CD83_-510mut 3$^{rd}$ IRF-Site". Combinations of the 3 IRF-site mutations resulted in constructs, bearing 1, 2 or 3 mutated IRF-sites:

mut: mutated pGL3/UPPmut 3$^{rd}$ IRF-Site
pGL3/P-510mut 3$^{rd}$ IRF-Site
pGL3/185 bp enh. s_as 1$^{st}$ IRF-site mut/P-510
pGL3/185 bp enh. s_as 2$^{nd}$ IRF-site mut/P-510
pGL3/185 bp enh. s_as 1$^{st}$/2$^{nd}$ IRF-site mut/P-510
pGL3/185 bp enh. s_as 1$^{st}$/2$^{nd}$ mut/P-510mut 3$^{rd}$ IRF-Site } These constructs were subsequently extended with the spacer sequence "S1"

TABLE 8

Cloned luciferase reporter constructs with mutated IRF-sites

| Donor/template | Excision method | Insert | Recipient | Result |
|---|---|---|---|---|
| GENEART standard vector/CD83_-510mut 3rd IRF-Site | Restriction digest; NheI/XhoI | P-510mut 3rd IRF-Site | pGL3/MP-261 NheI/XhoI | pGL3/P-510mut 3rd IRF-Site |
| GENEART standard vector/CD83_-510mut 3rd IRF-Site | Restriction digest; NheI/SmaI (blunt) | UPPmut 3rd IRF-Site | pGL3/Basic; NheI/XhoI (blunt) | pGL3/UPPmut 3rd IRF-Site |
| pGL3/185bp enh. s/MP-261 | PCR; KpnI | 185 bp enhancer 1st IRF-site mut | pGL3/P-510; KpnI | pGL3/185bp enh. s_as 1st IRF-site mut/P-510 |
| pGL3/185bp enh. s/MP-261 | PCR; KpnI | 185 bp enhancer 2nd IRF-site mut | pGL3/P-510; KpnI | pGL3/185bp enh. s_as 2nd IRF-site mut/P-510 |
| pGL3/185bp enh. s/MP-261 | PCR; KpnI | 185 bp enhancer 1st/2nd IRF-site mut | pGL3/P-510; KpnI | pGL3/185bp enh. s_as 1st/2nd IRF-site mut/P-510 |
| pGL3/185bp enh s/MP-261 | PCR; KpnI | 185 bp enhancer 1st/2nd IRF-site mut | pGL3/P-510mut 3rd IRF-Site; KpnI | pGL3/185bp enh. s_as 1st/2nd mut/P-510mut 3rd IRF-Site |
| RP3-380E11 | PCR; SacI/MluI | S1 | pGL3/P-510mut 3rd IRF-Site; SacI/MluI | pGL3/P-510mut 3rd IRF-Site + S1 |
| RP3-380E11 | PCR; SacI/MluI | S1 | pGL3/185bp enh. s_as 1st IRF-site mut/P-510; SacI/MluI | pGL3/185bp enh. s_as 1st IRF-site mut/P-510 + S1 |
| RP3-380E11 | PCR; SacI/MluI | S1 | pGL3/185bp enh. s_as 1st/2nd IRF-site mut/P-510; SacI/MluI | pGL3/185bp enh. s_as 1st/2nd IRF-site mut/P-510 + S1 |
| RP3-380E11 | PCR; SacI/MluI | S1 | pGL3/185bp enh. s_as 1st/2nd mut/P-510mut 3rd IRF-Site; SacI/MluI | pGL3/185bp enh. s_as 1st/2nd mut/P-510mut 3rd IRF-Site + S1 |

8. Primers

All primers were purchased from MWG Eurofins Operon (Ebersberg).

Notes and Abbreviations:
fw, for: DNA oligonucleotides in forward orientation
rev: DNA oligonucleotides in reverse orientation
mt: mutant
wt: wild type
aa: amino acid The original IRF-2 PCR template (EF1α/IRF-2) provided by Kay Childs (Division of Basic Medical Sciences St. George's, University of London, U.K.) contained 3 defective aa (3, 4, 5). First the defective sequence was subcloned via PCR (primers: IRF-2 fwd HindII; IRF-2 rev XbaI) in pCDNA 3.1 and from that template a PCR product with the corrected sequence was generated by using PCR mutagenesis (primers: IRF-2mut; fwd IRF-2mut rev;).

Cloning Primers for Luciferase Reporter Constructs

TABLE 9

Cloning primers for luciferase reporter constructs

| Primer (SEQ ID NO:) | Sequence | Description |
|---|---|---|
| A-1 (6) | 5'-GGCGGTACCAGCTGGGGCTCTTCTCAATATTATAAAG-3' | Fragment C deletion; rev; wt |
| A-10 (7) | 5'-GGCGGTACCAGATGATTTCCAAAGGAAGGGAG-3' | Fragment C deletion; fw; wt |
| A-1b (8) | 5'-GGCGGTACCCAATATTATAAAGTCTATTTATAG-3' | Fragment C deletion; 185 bp enhancer; rev; wt |

TABLE 9-continued

Cloning primers for luciferase reporter constructs

| Primer (SEQ ID NO:) | Sequence | Description |
| --- | --- | --- |
| A-2 (9) | 5'-GGCGGTACCAGGTGCCAATGGGGACAGTACG-3' | Fragment C deletion; rev; wt |
| A-3 (10) | 5'-GGCGGTACCAGAAGGCATTGCAACTCTGG-3' | Fragment C deletion; |
| A-4 (11) | 5'-GGCGGTACCGATGCTTCACTCTCCTCACC-3' | Fragment C deletion; rev; wt |
| A-8 (12) | 5'-GGCGGTACCAGTACTTTGGGCCTGGTTGATAATC-3' | Fragment C deletion; fw; wt |
| A-9 (13) | 5'-GGCGGTACCCCTATGGGTGATGCAAAACGAAAG-3' | Fragment C deletion; 185 bp enhancer; fw; wt |
| C-forward (14) | 5'-CCAGGGTACCGAGGAGGTATTTTGAGAAAATATG-3' | CD83 intron 2 fragment C fw; wt |
| C-forward 2 (15) | 5'-CCAGGGTACCACAATATCATGTCTGTGAGGAGTAAAGC-3' | Fragment C deletion; fw; wt |
| C-Kurz 1 (16) | 5'-GGCGGTACCTATAATATTGAGAAGAGCCC-3' | Fragment C deletion; fw; wt |
| C-Kurz 2 (17) | 5'-GGCGGTACCATTGGCACCTATAGTACTTG-3' | Fragment C deletion; fw; wt |
| C-Kurz 3rev (18) | 5'-GGCGGTACCCTTACGCCTGTAATCCCAGC-3' | Fragment C deletion; rev; wt |
| C-reverse (19) | 5'-GCAGGGTACCTTCCTCTTCTTTGTGTAGTG-3' | CD83 intron 2 fragment C rev; wt |
| Intron2-A_for (20) | 5'-TTAAGGTACCGTAGGTGCTGCGATACC-3' | CD83 intron 2 fragment A; fw; wt |
| Intron2-A_rev (21) | 5'-CCGGGGTACCAATGAAGTAGGAATATTTAAC-3' | CD83 intron 2 fragment A; rev; wt |
| Intron2-B_for (22) | 5'-CATTGGTACCTTACTTACTGTGGGATCAGAG-3' | CD83 intron 2 fragment B fw; wt |
| Intron2-B_rev (23) | 5'-GCAAGGTACCAAAGAACCACATCTATTACAAC-3' | CD83 intron 2 fragment B rev; wt |

Cloning Primers for the Mutated 185 bp Enhancer

TABLE 10

Cloning primers for the mutated 185 bp enhancer luciferase reporter constructs.

| Primer (SEQ ID NO:) | Sequence | Description |
|---|---|---|
| 185 bp Enh.fw/MT (24) | 5'-GGCGGTACCCCTATGGGTGATGCAGGACTATAGAGG ATATATGGTG-3' | 185 bp enhancer; fw; $1^{st}$ IRF-site mt |
| 185 bp Enh.fw/WT (25) | 5'-GGCGGTACCCCTATGGGTGATGCAAAACGAAAGAGG ATATATGGTG-3' | 185 bp enhancer; fw; wt |
| 185 bp Enh.rev/MT (26) | 5'-GGCGGTACCCAATATTATAAAGTCTATTTATAGTAGAC TTTTATATGAAGTCACACTCTTATTCCTCTCCTCTCCC-3' | 185 bp enhancer; rv; $2^{nd}$ IRF-site mt |
| 185 bp Enh.rev/WT (27) | 5'-GGCGGTACCCAATATTATAAAGTCTATTTATAGTAGA CTTTTATATGAAGTCACACTCTTACTTCCCTTTTCTCCC-3' | 185 bp enhancer; rev; wt |

Example 1: CD83 is Upregulated During DC Maturation and is not Expressed by HFF Cells FIG. 1, (A): One hundred thousand day 5 iDCs, 20 h LPS-matured DCs and HFF cells for each setup were harvested and stained with PE-labeled mouse anti-human CD83 mAB or mouse IgG1 isotype-control for flow cytometric analyses. Each quadrangle represents $1 \times 10^4$ living cells determined by a gate on forward and side light scatter and PI-staining. In each histogram plot the black line represents mean fluorescence intensity of the isotype-control stained cells and the red line represents mean florescence intensity of the anti-CD83 stained cells. (B): One million day 5 iDCs or HFF cells per well were seeded in a 12-well tissue culture plate. Immature DCs were either matured for 3 h, 6 h, 10 h and 24 h or left untreated as the HFF cells. Cells were lysed in RIPA buffer at the indicated time points. For Western blot 20 µg per lane of whole cell lysates from either immature DCs, maturing DCs (3-24 h after addition of LPS) or HFF cells were loaded on a denaturing 12.5% SDS polyacrylamide gel and blotted afterwards onto a nitrocellulose membrane. The membranes were incubated with a rat anti-human CD83 and a mouse anti-human GAPDH primary antibody and subsequently with an anti-rat HRP-conjugated or an anti-mouse HRP-conjugated secondary antibody, respectively. The signal was detected via chemiluminescence that was visualized on a photo film. (C) Total RNA was isolated from iDCs, 20 h LPS-matured DCs and HFF cells using a QIAshredder and RNeasy Mini Kit (Quiagen) according to the manufacturer's instructions and reversely transcribed with an Oligo $(dT)_{12-18}$ primer. Afterwards PCR was performed with an intron spanning primer pair for CD83 and a control primer pair for GAPDH. Additionally, one PCR reaction was prepared with water instead of DNA as a negative control.

Example 2: Schematic Depiction of the CD83 Gene Locus and the Respective Acetylation Data Resulting from the ChIP-Chip™ Microarray Analysis FIG. 2, (A): Schematic depiction of the CD83 genelocus and nucleotide positions on chromosome 6. Coding sequence depicted in blue (CDS), exons in grey (E1-E5) and introns in red (I1-I4). (B) Data for the CD83 hyperacetylation were provided by NimbleGen Systems and interpolated subsequently over a space of 500 bp using the Signal Map software. (C) Overlay of the interpolated data for mature DCs aligned with the positions of the CD83 exons (black; E1-E5) and introns (red; I1-I4)

Example 3: Schematic Depiction of Constructs for Gene Reporter Assays

FIG. 3: A pGL3 vector backbone only coding for the luciferase gene and lacking any regulatory element (pGL3/Basic) was used for background control. The pGL3 backbone containing the luciferase gene driven by a CMV promoter (pGL3/CMV/luc) was generated for its usage as a positive control and for internal normalization. The same plasmid coding for GFP instead of luciferase (pGL3/CMV/GFP) was used to determine transfection efficiency. As reference control a pGL3 plasmid coding for the luciferase gene driven by the CD83 minimal promoter MP-261 (pGL3/MP-261) was generated. Finally, plasmids containing a putative regulatory element in both orientations upstream of the MP-261 (pGL3/Put. reg./MP-261) were generated to study its effects on the MP-261.

Example 4: Schematic Depiction of the Subcloning Strategy of the Hyperacetylated Region of CD83 Intron 2

FIG. 4: The first 6 kb of CD83 intron 2 were subdivided into 3 fragments A (1239 bp), B (2359 bp), and C (2220 bp). After PCR amplification each fragment was subcloned in sense and antisense orientation upstream the MP-261 into the pGL3/MP-261 plasmid. Hyperacetylated regions are depicted as blue bars, exons as black bars (E1-E5) and introns are marked in red (I1-I5). The red boxes indicate the base pair position relatively to the transcription start (bp 1).

Example 5: Fragment C Enhances the MP-261 Activity Specifically in XS52 Cells

FIG. 5: Two hundred thousand XS52, NIH3T3 or HeLa cells per well were seeded in a 12-well tissue culture plate and were grown overnight at 37° C., 5% $CO_2$. The next day, the cells were transfected with 2.5 µg of reporter plasmids containing fragment A, B or C of the CD83 intron 2 in sense (s) or antisense (as) orientation upstream of the MP-261 or the pGL3/MP-261 as reference control using the DEAE-Dextran method. As controls the pGL3/Basic and the pGL3/CMV/luc vector were transfected to assess background activity and for internal normalization, respectively. The promoter activity was determined by luciferase reporter assays 48 h after transfection. The resulting RLUs were further normalized to the protein concentration of each lysate. The plasmids containing fragments A, B and C were compared to the pGL3/MP-261 vector for each cell line and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 6: Schematic Depiction of the Deletion Mutants C1-C14 of Fragment C

FIG. 6: The deletion mutants C1-C14 of the CD83 intron 2 fragment C were generated by PCR amplification and cloned in sense (s) and antisense (as) orientation into the pGL3/MP-261 reporter plasmid upstream of the MP-261. Induction of the minimal promoter activity was determined in XS52, NIH3T3 and HeLa cell lines by luciferase reporter assays. Induction is depicted relatively to the activity of the pGL3/MP-261. --- no induction of the MP-261, + weak induction of the MP-261, ++ medium induction of the MP-261; +++ strong induction of the MP-261.

Example 7: The 185 bp Long Deletion Mutant C13 of Fragment C Enhances the MP-261 Activity Specifically in XS52 Cells FIG. 7: Two hundred thousand XS52, NIH3T3 or HeLa cells per well were seeded in a 12-well tissue culture plate and were grown overnight at 37° C., 5% $CO_2$. The next day, cells were transfected with 2.5 µg of either pGL3/MP-261 reporter plasmids containing the deletion mutants C1-C14 of the fragment C of the CD83 intron 2 in sense (s) or antisense (as) orientation upstream of the MP-261 or the pGL3/MP-261 as reference control using the DEAE-Dextran method. As controls the pGL3/Basic and the pGL3/CMV/luc vector were transfected to assess background activity and for internal normalization, respectively. The promoter activity was determined by luciferase reporter assays 48 h after transfection. The resulting RLUs were further normalized to the protein concentration of each lysate. The plasmids containing the different fragments were compared to the pGL3/MP-261 vector for each respective cell line and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 8: Fragment C and the 185 bp Enhancer Induce the MP-261 Activity Specifically in mDCs FIG. 8: Two million day 5 iDCs were electroporated with 4 µg of either pGL3/Basic, pGL3/MP-261, pGL3/FragmentC/MP-261 s/as or pGL3/185 bp Enh. (C13)/MP-261 s/as luciferase reporter plasmid using the AMAXA technology. Afterwards, cells were transferred to a 12-well tissue culture plate and split into two equal fractions. One of the fractions was matured 3 h after electroporation with LPS to a final concentration of 0.1 ng/ml and the other fraction was replenished with growth medium without LPS. Cells were then grown at 37° C., 5% $CO_2$ for 20 h. The pGL3/Basic and the pGL3/CMV/luc vector were electroporated to assess background activity and for internal normalization, respectively. The promoter activity was determined by luciferase reporter assays and the resulting RLUs were normalized to the protein concentration of each lysate. The plasmids containing the different fragments were compared to the pGL3/MP-261 vector and the resulting p-values were determined via one way ANOVA and Bonferroni's Multiple Comparison post hoc test. *$p<0.05$, $p<0.01$, *$p<0.001$. Results depict the means (±SEM) of four independently performed experiments representing four different donors in (A) and three experiments representing three different donors in (B).

Example 9: Neither Fragments A, B, C Nor the 185 bp Enhancer Induce the MP-261 in Raji and Jurkat Cells FIG. 9: Ten million Raji or Jurkat cells were electroporated with 20 µg of reporter plasmids containing fragment A, B, C or the 185 bp enhancer in sense (s) or antisense (as) orientation upstream of the MP-261 or the pGL3/MP-261 as reference control using a Genepulser II. As controls the pGL3/Basic and the pGL3/CMV/luc vector were electroporated to assess background activity and for internal normalization, respectively. After electroporation, cells were transferred into 10 ml prewarmed growth medium and cultivated at 37° C., 5% $CO_2$ for 24 h. The promoter activity was determined by luciferase reporter assays and the resulting RLUs were further normalized to the protein concentration of each lysate. The plasmids containing the different fragments were compared to the pGL3/MP-261 vector for each respective cell line and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 10: Presumed Biocomputational Model for the Interaction of the CD83 Upstream Promoter, the MP-261 and the 185 bp Enhancer FIG. 10, (A): Depiction of the three regulatory elements with the predicted transcription factor binding sites regulating CD83 transcription: (i) The upstream promoter (UpP) containing NFκB-sites 1 and 2, IRF-site 3 and one SP1 site, (ii) the 261 bp long CD83 minimal promoter (MP-261) containing NFκB-sites 3, 4 and 5 and four SP1-sites and (iii) the 185 bp enhancer containing IRF-sites 1 and 2 as well as one SP1-site. The UpP and the MP-261 including the 82 bp naturally occurring spacer sequence are termed 510 bp promoter (P-510). Previously confirmed and published transcription factor binding sites are marked with a red arrow. (B): Designated interaction of the 185 bp enhancer with the MP-261 mediated by the interaction of IRF-sites 1 and 2 with NFκB-sites 3 and 5, respectively. (C): Ternary complex formation with the UpP as third interaction partner. The interaction between the UpP and the MP-261 is mediated by IRF-site 3 and NFκB-site 4.

Example 11: Schematic Depiction of Reporter Constructs Containing the UpP and the Spacer Sequence S1

FIG. 11: The P-510 as well as the CD83 upstream promoter (UpP) were cloned upstream of the luciferase gene into the pGL3/Basic plasmid, thus generating pGL3/P-510 and pGL3/UpP, respectively. The UpP comprised in the P-510 is highlighted in purple. Furthermore, a 500 bp long spacer sequence (S1) was inserted in between MP-261 and P-510 generating the plasmids pGL3/185 bp Enh./S1/MP-261 and pGL3/185 bp Enh./S1/MP-261, respectively. The spacer sequence was also introduced into the plasmids pGL3/MP-261 and pGL3/P-510, resulting in the plasmids pGL3/S1/MP-261 and pGL3/S1/P-510.

Example 12: The Spacer Sequence S1 does not Significantly Affect the Induction of the MP-261 and the P-510 in XS52 Cells FIG. 12: Two hundred thousand XS52, NIH3T3 and HeLa cells per well were seeded in a 12-well tissue culture plate and were grown overnight at 37° C., 5% $CO_2$. The next day, cells were transfected with 2.5 µg of either pGL3/MP-261 or pGL3/P-510 with or without the 185 bp enhancer in sense (s) or antisense (as) orientation either containing the spacer sequence 51 or not, using the DEAE-Dextran transfection method. As controls the pGL3/Basic and the pGL3/CMV/luc vector were transfected to assess background activity and for internal normalization, respectively. The promoter activity was determined by luciferase reporter assays 48 h after transfection. The resulting RLUs were further normalized to the protein concentration of each lysate. The plasmids containing the spacer sequence S1 were compared to the corresponding plasmids without the spacer sequence for each respective cell line. The resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 13A: The Spacer Sequence S1 does not Significantly Affect the Induction of the MP-261 in mDCs FIG. 13, (A): Two million day 5 iDCs were electroporated with 4 µg of either pGL3/MP-261 with or without the 185 bp enhancer in sense (s) or antisense (as) orientation upstream of the MP-261 or with their respective counterparts comprising the spacer sequence S1, using the AMAXA technology. Afterwards, cells were transferred to a 12-well tissue culture plate and split into two equal fractions. Cells were matured 3 h after electroporation with LPS to a final concentration of 0.1 ng/ml and were then cultured at 37° C. in a humidified atmosphere at 5% $CO_2$ for 20 h. As controls the pGL3/Basic and the pGL3/CMV/luc vector were electroporated to assess background activity and for internal normalization, respectively. The promoter activity was determined by luciferase reporter assays. The resulting RLUs were further normalized to the protein concentration of each lysate. The plasmids containing the spacer sequence S1 were compared to the corresponding plasmids lacking the spacer sequence. The resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of five independently performed experiments representing different donors.

Example 13B: The Spacer Sequence S1 does not Significantly Affect the Induction of the P-510 in mDCs FIG. 13, (B): The cells were treated and electroporated in the same way as in (A), but instead of plasmids bearing the MP-261, plasmids comprising the P-510 were used. The resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments representing different donors.

Example 14: The Ternary Complex of UpP, MP-261 and 185 bp Enhancer Shows a Specific Transcriptional Induction in mDCs FIG. 14, (A): One million day 5 iDCs per well were seeded in a 12-well tissue culture plate in 250 µl medium supplemented with 800 U/ml GM-CSF and 500 U/ml IL-4. Recombinant adenovirus as indicated at 500 $TCID_{50}$/cell in a final volume of 250 µl medium without cytokines was added to the cells. After 1.5 h of incubation at RT, 2.5 ml of growth medium replenished with cytokines as described before was added per well. For the generation of mDCs LPS was added 3 h after transduction to final concentration of 0.1 ng/ml. The promoter activity was determined by luciferase reporter assays 24 h after transduction. As controls the Ad5luc1 was transduced for internal normalization. The resulting RLUs were further normalized to the protein concentration of each lysate. The transduction setups were compared to the transduction of Ad261/S1 and the resulting p-values were determined via one way ANOVA and Bonferroni's Multiple Comparison post hoc test. *$p<0.05$, $p<0.01$, *$p<0.001$. Results represent the means (±SEM) of three independently performed experiments representing different donors.

Example 15: The Ternary Complex of UpP, MP-261 and 185 bp Enhancer Shows No Specific Transcriptional Induction in Raji, Jurkat and JCAM Cells FIG. 15, (A)-(C): One million Raji, Jurkat and JCAM cells per well were seeded in a 12-well tissue culture plate in 250 µl RPMI1640 supplemented with 2% FCS. Recombinant adenovirus as indicated at 500 $TCID_{50}$/cell for Jurkat and JCAM and 50 $TCID_{50}$/cell for Raji in a final volume of 250 µl RPMI1640 supplemented with 2% FCS was added to the cells. After 1.5 h of incubation at RT, 2.5 ml of appropriate full growth medium was added per well. Raji cells were either stimulated 3 h after transduction with LPS to a final concentration of 0.1 ng/ml or left untreated. Jurkat and JCAM cells were either stimulated 3 h after transduction with $PGE_2$ and TNF-α to a final concentration of 1 µg/ml and 10 ng/ml, respectively, or left untreated. The promoter activity was determined by luciferase reporter assays 24 h after transduction. As additional controls Ad5luc1 was transduced for internal normalization. The resulting RLUs were further normalized to the protein concentration of each lysate. The transduction setups were compared to the transduction of Ad261/S1 and the resulting p-values were determined via one way ANOVA and Bonferroni's Multiple Comparison post hoc test. *$p<0.05$, $p<0.01$, *$p<0.001$. Results represent the means (±SEM) of three independently performed experiments.

Example 16: Schematic Depiction of Reporter Constructs Containing Mutated IRF-Sites Used for Luciferase Assays FIG. 16: To generate the pGL3/UpP plasmid, the CD83 upstream promoter a 244 bp fragment of the P-510 containing the UpP was isolated by enzymatic digestion and cloned upstream of the luciferase gene into the pGL3/Basic plasmid. The individual IRF-sites in the pGL3/UpP, the pGL3/S1/P-510 and the pGL3/185 bp Enh./S1/P-510 plasmids were mutated by PCR mutagenesis. The IRF-sites were mutated in different combinations in concordance with the point mutations in the EMSA control oligonucleotides.

Example 17: Mutation of any of the Three IRF-Sites in the Ternary Complex Significantly Reduces the Luciferase Expression in XS52 Cells FIGS. 17, (A) and (B): Two hundred thousand XS52 cells per well were seeded in a 12-well tissue culture plate and were grown overnight at 37° C., 5% $CO_2$. The next day, cells were transfected with 2.5 µg of the wildtype pGL3/UpP or the pGL3/S1/P-510 with and without the 185 bp enhancer in sense (s) or antisense (as) orientation upstream of the P-510 or with the analogical plasmids with one, two or three mutated IRF-sites using the DEAE-Dextran transfection method. The promoter activity was determined by luciferase reporter assays 48 h after transfection. As controls the pGL3/Basic and the pGL3/CMV/luc vector were transfected to assess background activity and for internal normalization, respectively. The resulting RLUs were normalized to the protein concentration of each lysate. The plasmids containing the different mutations were compared to the respective wildtype control and the resulting p-values were determined via one way ANOVA and Bonferroni's Multiple Comparison post hoc test. The mutated IRF-sites are indicated by their respective numbers. *$p<0.05$, $p<0.01$, *$p<0.001$ and n.s. not significant ($p>0.05$). Results represent the means (±SEM) of three independently performed experiments.

Example 18: Mutation of any of the Three IRF-Sites in the Ternary Complex Significantly Reduces the Luciferase Expression in mDCs FIG. 18: Two million day 5 iDCs were electroporated with 4 µg of either wildtype pGL3/S1/P-510 with and without the 185 bp enhancer in sense (s) or antisense (as) orientation upstream of the P-510 or with the analogical plasmids with one, two or three mutated IRF-sites, using the AMAXA technology. Afterwards, cells were transferred to a 12-well tissue culture plate and split into two equal fractions. Cells were matured 3 h after electroporation with LPS to a final concentration of 0.1 ng/ml and were then cultured at 37° C. in a humidified atmosphere at 5% $CO_2$ for 20 h. The promoter activity was determined by luciferase reporter assays 48 h after transfection. As controls the pGL3/Basic and the pGL3/CMV/luc vector were transfected to assess background activity and for internal normalization, respectively. The resulting RLUs were further normalized to the protein concentration of each lysate. The plasmids containing the different mutations were compared to the respective wildtype control and the resulting p-values were determined via one way ANOVA and Bonferroni's Multiple Comparison post hoc test. The mutated IRF-sites are indicated by their respective numbers. *$p<0.05$, $p<0.01$, *$p<0.001$ and n.s. not significant ($p>0.05$). Results represent the means (±SEM) of three independently performed experiments from different donors.

Example 19: Transcription Factors of the NFκB Family and IRF-5 Induce the MP-261 in 293T Cells FIGS. 19, (A) and (B): Sixty thousand 293T cells per well were seeded in a 24-well tissue culture plate and grown overnight at 37° C., 5% $CO_2$. The next day, cells were cotransfected with 0.05 µg of pGL3/MP-261 reporter plasmid and 0.15 µg of each plasmid coding for the indicated transcription factors (p50, p65, cRel or IRF-5 in pCDNA3.1) or empty vector backbone as control. The total amount of DNA was adjusted with pCDNA3.1 empty vector backbone to 0.5 µg. For transfection the Lipofectamine™ LTX system was used. The promoter activity was determined by luciferase reporter assays 48 h after transfection. As controls the pGL3/Basic and the pGL3/CMV/luc vector were transfected to assess background activity and for internal normalization, respectively. The resulting RLU were further normalized to the protein concentration of each lysate. The cotransfections were compared to the pGL3/MP-261 control and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 20A: p65 and IRF-5 Induce the UpP in 293T Cells

FIG. 20, (A): Sixty thousand 293T cells per well were seeded in a 24-well tissue culture plate and grown overnight at 37° C., 5% $CO_2$. The next day, cells were cotransfected with 0.05 µg of pGL3/UpP reporter plasmid and 0.15 µg of each plasmid coding for the indicated transcription factors (p50, p65 and IRF-5 in pCDNA3.1) or empty vector backbone as control. The total amount of DNA was adjusted with pCDNA3.1 vector backbone to 0.5 µg. The promoter activity was determined by luciferase reporter assays 48 h after transfection. As controls the pGL3/Basic and the pGL3/CMV/luc vector were transfected to assess background activity and for internal normalization, respectively. The resulting RLU were further normalized to the protein concentration of each lysate. The cotransfections were compared to the pGL3/UpP control and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Example 20B: The Induction of the UpP by p65 and IRF-5 is Abrogated when the IRF-Site 3 is Mutated FIG. 20, (B): The cells were transfected as described in (A) either with 0.05 µg pGL3/UpP or pGL3/UpP 3.IRFmut reporter plasmid alone or cotransfected with 0.15 µg of each indicated transcription factor (p65 and IRF-5 in pCDNA3.1). The total amount of DNA was adjusted with pCDNA3.1 vector backbone to 0.5 µg. The pGL3/UpP and pGL3/UpP 3.IRFmut setups were compared and the resulting p-values were determined via one way ANOVA and Bonferroni's Multiple Comparison post hoc test. *$p<0.05$, $p<0.01$, *$p<0.001$ and n.s. not significant ($p>0.05$). Results represent the means (±SEM) of three independently performed experiments.

Sequence Listing, Free Text

| SEQ ID NO: | Description |
|---|---|
| 1 | Genomic sequence of the CD83 promoter of NT_007592.15; UpP bp 2531-2696, intermediate sequence bp 2697-2779, MP-261 bp 2780-3040, and 185 bp enhancer bp 7218-7402 |
| 2 | Upstream promoter (UpP) |
| 3 | Intermediate sequence |
| 4 | CD83 Minimal Promoter (MP-261) |
| 5 | 185 bp enhancer |
| 6-27 | Primers |
| 28-29 | Promoter regions of vectors pGL3/-510/S1/Es and pGL3/-510/S1/Eas, respectively |

The invention claimed is:

1. A CD83 promoter sequence comprising the CD83 Upstream promoter (UpP) sequence of SEQ ID NO:2, the CD83 Minimal Promoter (MP) sequence of SEQ ID NO:4 and the CD83 enhancer sequence of SEQ ID NO:5, or variants of said sequences having 98% homology over their entire length and/or being N- and/or C-terminally truncated by up to 10 nucleotides and having promoter activity, said UpP sequence being located 50 to 200 nucleotides upstream of said MP sequence and said enhancer sequence being located 200 to 4000 nucleotides upstream of the UpP sequence or 200 to 4000 nucleotides downstream of said MP sequence.

2. The CD83 promoter sequence of claim 1, wherein
   (i) the distance between the UpP sequence and the MP sequence is 70 to 120 nucleotides; and/or
   (ii) the distance between the UpP sequence/MP sequence and the enhancer is 250 to 750 nucleotides.

3. The CD83 promoter sequence of claim 1, wherein
   (i) the UpP sequence has SEQ ID NO:2;
   (ii) the MP sequence has SEQ ID NO:4; and/or
   (iii) the CD83 enhancer sequence has SEQ ID NO:5.

4. The CD83 promoter sequence of claim 3, wherein
   (i) the UpP sequence is linked to the MP sequence by the intermediate sequence of SEQ ID NO:3 or a variant thereof having 95% homology to SEQ ID NO:3 over its entire length; and/or
   (ii) the CD83 enhancer sequence is located 450 to 550 nucleotides upstream to the UpP sequence or 450 to 550 nucleotides downstream of the MP sequence.

5. The CD83 promoter sequence of claim 1, which
   (i) comprises the sequence of nucleotides 29-1259 of SEQ ID NO:28 or the sequence of nucleotides 27-1257 of SEQ ID NO:29; and/or
   (ii) is human dendritic cell-specific.

6. A vector or viral vector comprising the CD83 promoter sequence according to claim 1.

7. The vector or viral vector of claim 6, wherein
   (i) the CD83 promoter sequence is functionally linked to a gene of interest; and/or
   (ii) the viral vector is an adenoviral vector.

8. A cell, tissue culture or transgenic non-human organism, which comprises the CD83 promoter sequence according to claim 1.

9. The cell of claim 8, which is a dendritic cell.

10. A method for producing dendritic cells ex vivo, said method comprising introducing a vector or viral vector of claim 6 into a DC progenitor cell.

11. Transfection reagent comprising the vector or viral vector of claim 6.

12. A vector or viral vector comprising (i) the CD83 promoter sequence according to claim 1 functionally linked to (ii) a gene of interest.

13. A CD83 promoter sequence comprising the CD83 Upstream promoter (UpP) sequence of SEQ ID NO:2, the CD83 Minimal Promoter (MP) sequence of SEQ ID NO:4 and the CD83 enhancer sequence of SEQ ID NO:5, said UpP sequence being located 50 to 200 nucleotides upstream of said MP sequence and said enhancer sequence being located 200 to 4000 nucleotides upstream of the UpP sequence or 200 to 4000 nucleotides downstream of said MP sequence.

* * * * *

SEQUENCE LISTING

<160> NUMBER OF SEQ ID NOS: 29

<210> SEQ ID NO 1
<211> LENGTH: 8540
<212> TYPE: DNA
<213> ORGANISM: Homo sapiens

<400> SEQUENCE: 1

```
ggcttaagcg atcctcctgc ctcagcctcc tgagtagctg ggaccacagg tgcaagccac      60
catgcccggc tattttctgt atttgttatt tttttgcatt tttagtaaag accaggttca     120
ccatgttgcc caggccagtc ttgaactcct aatctcaagt gatccgtcca cctgggcctt     180
ccaaagtgct gggattacag gcgtgagcca ctgcacccag ccaccagaac gattttgaag     240
acgaagttca acatgtgagg actcacttcc accacagcaa gacttaatta aattatagta     300
ataagaaagt gtgatattag cacaaagaga ggcagaatag agtctagaaa caggcccact     360
catatgtaga aatttgtata aagcacagat gtcattttaa atcagtaggg aaagaaggac     420
ttttagcaag cagcattgga aaaaatggtt atccatatgg aaaaaataag ttagatcacg     480
acatcaaacc atatttaaat ggattaaaga ccaacatatg aaaaagcatg actttaaaag     540
ttttggaagg aaatgaagga gaatgttttt atgatctcag gtcaggaaaa gatttcttaa     600
acacaatacc agaagcacaa atcataaacc aaaagatcag taaatttgac cacatgaaaa     660 tatttttttaa aaactctttg gtaaattaaa gatatcataa acaaaatgga aaatacaaat     720
cttaaacttg gagaagagat ttggcatgga tataaccaag aaaggatttg gcccagattt     780
tataaacagc gctcatggaa aaggccaaag gatatgaatg acaatgctca gaaatatcca     840
atgttcttga agcatatgtt atcaatgtaa cataaattaa gcaaaaagga tctaatattt     900
cacactcatt agataggcag aaatttaaaa agatctggct gggcacgtgg ctcacacctg     960
taatcccagt accttgggag gccaaggtag gaggatctct tgagcccagg aatttgagac    1020
cagcctgagc aacatagtga gaccctatct ttaaagaaaa aaatctgatc atgctaagac    1080
ctgctgaggg gagtgtaaat gggcatgtgc attttggata ataagacggc aatatttaac    1140
aatgcagtgt aattactgag ctagagtgtt ggaagacttt cagctcccct gcaacattgt    1200
ttataatcag gaaaaactga aaagaagcat aaatggctag gtatgagatc tggcagagga    1260
cacatagtgg gtctcaaaag accatcctgg ctaacacggt gaaacccgt  ctaaaaatac    1320 acacacaaaa aaattagtcg ggcgtggtgg cgggctcctg tagtcccagc tactcgggag    1380
gctgaggcag gagaatggcg tgaacccggg aggcggagct tgcagtaagc tcagatcacg    1440
gccactgcac tccagcctgg gagacagatc gagactccgt ctcaaaaaaa aaaaaaaaa    1500 aaaaaaaaga gggtctcgaa aatgttagta ctgttttatt tctcaagaat aaattgtata    1560
cagatgtgtt caattccata ttttctatac ttattttgta tgcttaacat tttcacaatt    1620
```

```
aaaaaattaa tttggtgagg ctgctggaga aaaggtactc acacaagctg gcgggactgt    1680
caattgatat aactacttcc aagagcagat tagaactggt ggtatagtga tgccactctt    1740
tttaacctct tggatggaca agatagaaa ggttggataa cagtttgtgt tggcaaacag     1800
gcactctctt tgcagatggg aatatagatt gaagacacct ccttgcaggt aatttttgg     1860 caatatttga caaaattgga aactcccctt cacctagcac aatttccttg aggtatttat   1920
tctaagaaaa taagcaattt tagagcaaag atttatctac actgaagttt cccatagcaa   1980
tcacagtatt gtttctaata ttagtaatac aaaagaaac aacctgtatg tctaacacta    2040
atcgattcta atttatggtg caactgaaca atggaccaaa atgatgctgt tggaagtttt   2100
taatgatgtg gaaccgcttg caaattatta agctaaaaga aagtaggtta caagatagca   2160
ggaagaataa accattaaaa ataccaatct gtgcactgac aaatgttata aatattttac   2220
gttatgttat gttataaaca ttttataata taaaaaaatg ttaactgaag ttacttcctg   2280
gatgaattac aggtgatttc attgtcttct agaattttct tttccaaaaa tgttgtgtat   2340
gcgtgtaatt attattttaa taggagacac tctcctttgg tgatataatt taaacaggac   2400
ggtactgact gataacctcc cggggaaggc agggagccaa gtactacaga cttgtatgtt   2460
tccatggaaa tctaacgcgc cttttgattat cacagattct ggagaagagt gaggacttgg  2520
gttcaccagt gcgttcccaa ggacaggctg ggcttctgag gaagttgccc accctctcgg   2580
aatctggttt ggcctccgta aaatgggcag atcccgctcg gatggcccgg ttccggcctt   2640 cctttttgcgg gtcaacggca gcgtcacgcg cgcgagcgcg gtctgcaaag ccccagcgc   2700 tgggcgtcac gcggggattg ctgtcgccgc tgccagccgc agcagcgacg cgaactcggg   2760
gcgcccggcc cgggcgcgcg ggggcgggga cgcgcacgcg gcgagggcgg cgggtgcgac   2820
ggggggcggg acggggggcgg ggacggggggc gaagggggcg gggacggggg cgccccggcc 2880
taagcgggac taggagggcg cgccacccgc ttccgctgcc cgccggggaa tccccgggc    2940 tggcgcgcag ggaagttccc gaacgcgcgg gcataaaagg gcagccggcg cccgcgcgcc   3000
acagctctgc agctcgtggc agcggcgcag cgctccagcc atgtcgcgcg gcctccagct   3060
tctgctcctg agctgcggta gggctcgcga gcgcctgtct cgcctgtcgc ccccccgcccc 3120 tccacgacac ccctcccgt cggtcgcttg ctcacgacgc gctctctctt tcttgtagcc    3180
tacagcctgg ctcccgcgac gccggaggtg aaggtggctt gctccgaaga tgtggacttg   3240
ccctgcaccg ccccctggga tccgcaggtt ccctacacgg tctcctgggt caaggtaggt   3300
gctgcgatac ccacgggctg gggtttggtg ggctcatttg aagacagcag gaaccatctc   3360
ccctaggctg gcgaccctct gtggctgcca ggtgggggcg aggggcgtct cccgcagctg   3420
aacttggagt acccagcctc ccgtcgcgcc tcccccaccc catccgcatc caggtacagg   3480
gccgaattag gttttgctct ccgcagacct caatcccctt cctgtcactg aaggtggcct   3540
gagatgaatg atccacttaa gatgttttgg aagggcagag actctcattt ggattaattc   3600
tggaggccac ctgtggttgt gggccagcag gtcaggaaga aagcaacagg gacctagatt   3660
tgggcattgg acagggggaa tgtctccaga cttctgattt cttgtgtttt gtgactgtga   3720
tgcccatgat acatgggagg gggagggggc aatttgaaag gaaaggctaa gacacagaag   3780
tgacttaggc catttcatcc atggtagtta tcagtggtca tctcctttgt gggatccct    3840 tggcttcctc ccctagccct cctcctcctt cctctggcag ccttgagagc atcaggtgga   3900
tgcatgagcc ggagcccgca tgtgtaagaa caggccttgc tgctcctact gtaagtggac   3960
tgagtgacaa ggaggctttt tcaaggtttc ctcttgactg aaacattctc agattctaag   4020
```

```
atggcaatga tggtgtcatt ccaaagccaa gcagctactg tttgatatca ctggtccttc    4080
tttaagtcag gccactgcta ccacagcacc tccattttaa cccaaatgaa tatgatatta    4140
caaccttact ctgtagctct cactgatttg ctgtcttacc acgggggcaa atctctgcac    4200
ttgtagcttt ccccaaaatg cagggcgttc ttctgcccac cataaaagat actataagaa    4260
actgtacgtc tttggccact aacagtaca aggcatcatt gcggtgatct ctttgtgtgt     4320
gtgtctccta actggatggt cagttccctg ggggcagtg gctgtatcca tacttctgtg     4380
tattcttcac ggcacctaat ttttgcccta taaattgcaa aggtgctctg tgaattcagc    4440
ccagcacttc atgagttatg catgacgggg atggtgctgc tgcctcagag cattgtattg    4500
tgtataaaag taaggtgtta aatattccta cttcattggt accttactta ctgtgggatc    4560
agagaacaca acaattccga aattgttctc atagtcaaaa caatagtatt tttaaaaata    4620
ttgtaaaaac aattttgaa tgctcaccac gtgccaagct ccaaggtaaa tatttacata    4680
cattatccat ttccatccat cggaagaatg gacttaggga ttagtactgt tactattcct    4740
actttacagg tgaggaaact gagccttagg gagggaaata acttgtccac ttttgcacag    4800
ctagctaaat ggtggagttg ggatttgaac gaagcagtct gattccaaat cctgagttgt    4860
tagaggtcta tcttgatctc tgttttctcc cttaataact aagataaag aaaatcaaag     4920 tgcccctggg ctaaccaggc agggacttag ttatctcaaa gaacgggaa aaacatgaaa     4980 ccactatccc ttccagagag taactattta ataaagaaaa cattattaat accccagggg   5040
gagtaattaa aaagtactca tgaaacaagt agatgaaatt tcaggctgtg aagttcaaac   5100
agttctggag tgaaagcttc ttgcacaggg tcatttggaa tggtccacta aaccatagca   5160
attaaccttg gacttctcct tggatgtcag ctggtgacgt aactcggtaa cgcatgagct    5220
tgtttattgg acagaattct tgcgagattt acccccaagg tctttgaaag ctctgtcaag    5280 aaaaaaggg acagcagtct ctaggcgttc ttttttcct gttgatccat ggaatagtgc      5340
caatgaaaag tcataccgta gttatttttt gagaagtaaa tggtgattga gattcgtggg    5400
taggagagtt atgctatacc aataaacgaa tcaggtgcct cgaaagtgac atatattgtt    5460
cctttaagca tttttttaa aacagctctc agcatgttct gtagatactt attatttcc      5520 agcccaataa ttatactttt tcattgatta tgcttataca acaaaaatgg atagagtgtt   5580
ctggagacaa ggccagtggt gaaatgccaa aatacttcat tttacagaat gttaagcatc   5640
tggtcatttt tctataagtt tcttgtaaaa tgtttcatca aagtggaggg gtagccacaa   5700
agggaggaat ttcattttgg taaccagaac cagcttatcc catcctactc acttcatcat    5760
cactaccctg gctttgtaaa acctgttttg ccagcttagg aggggcttc atactgggca    5820 aggaaagcag agtcccttgc agtgggtttt caccatccac cagattgaag cacattctgc   5880
aggctgtctg catatcataa gtatggttat aatgactcac aatttaaaat tctattcacc   5940
actcaatcct ccggcaccat gtagcatctt gcctttgtcc atttggcact gatacttgta   6000
attaacaaaa ggacccatgt aaaccatgtg ttttttatca tatgcctttg accagaaaac   6060
tcaaaacaga cagcatccaa tctgtttgca acattagggt tgggaaggaa gagtgttcat    6120
tctgttctct ctgtttcaaa gatgcagtga gatgggctag aggggactta atagacacat   6180
gtgcaagagg ctaaaggtga agccaaaagt ggacagagat atcccaattc ctgttggccc    6240
agctcttctc ttctatggac catgtcctct taactgggat ccaacaaagg gtcctcttct    6300
catcccttcc tcccttatac ttttttaaggc ataatgggtg attgagaaga aatagaaaag   6360
```

```
ttaatacatt atattcatta ggatagtagc tcaatttagc tttatgttta ttttttgaga    6420
cagagtgtca ccctgtttcc caagctggag tacagtggca tgaagatggc tcactgcagc    6480
ctcgacttcc tgggctcgag taatcctccc acctcagcct cccaagtagc tgagactaca    6540
agggcgtacc accacacctg gctaattttt atgtttttaa ttttttgtag ggacaagatt    6600
tcaatacatt gcccaggctg gtctccaact cctgagctca agccatcctc ccacttcagc    6660
ctcccaaagt gctaggatta caggcatgag ccaatcgatt tatcttttaa agttgtaata    6720
gactgggtgt ggtggctgag gcttatgcct gtaatcccag cattttggga ggcgaagatg    6780
ggaggatcac ttgagcccag gagtttgagg ccagcctggg caatgcagtg agacctgtct    6840
ctaccaaaaa aaaaaaaaaa aaaaaaaaaa gttgtaatag atgtggttct ttgaggaggt    6900
attttgagaa aatatgcaaa tagactttga tccatgactt ttcttccact ggccatgacc    6960
tgtgattaaa ttccagcata aaagggcata gcacaatatc atgtctgtga ggagtaaagc    7020
catgcattaa agggctgcat gtggacttca tgaaaagcgt cgctgtgtct acactctctt    7080
taatgtaggt ttggagagag aggatgactt tggttggagt actttgggcc tggttgataa    7140
tcactaaaga tagtaatgag tgatcattta tcccagagtt gcaatgcctt cttgtatcat    7200
gctaggagcc ctgacagcct atgggtgatg caaaacgaaa gaggatatat ggtgtcatct    7260
ctgggtgatg ctgcgggggt gaggagagtg aagcatcaca agacaagtgc ccttttcaga    7320
tgatttccaa aggaagggag aaaagggaag taagagtgtg acttcatata aaagtctact    7380
ataaatagac tttataatat tgagaagagc cccagctggg gcagatcatg ggccatccat    7440
ggagtgttct gcttctgaca ttaacactaa ggaaactgtt ggagagcagg ttaatggctt    7500
gcgtgaggcc acttcaaaag ttcaaggctg tcttccgtgt atgttgctaa acttctttt    7560 ggtggagtta tgttttctgt ctctaccatc ttgtgtgata atgagctaca aaaccaggga    7620
tactgaggag agcagagtgc cttaggaggg cctagagttg ataagcggtt ggggcagatg    7680
taatctgtac agccagagac cttcatagcc catggaagga gccagtactg aacacttact    7740
gtgcttcctt gattccagaa tgattctgtt gtaaggtgga tttaagaaca tgttttagga    7800
caaaaaggaa acatttctac attaaatgta gaaccattga attatgaaaa caatgtatgt    7860
tagaattaaa aaaaaaaaat cgtactgtcc ccattggcac ctatagtact tgacctggtt    7920
gaatcacttt tatgggctcc tccctaggtc aaaccatgaa agatgtaaag ttgcttttca    7980
gatgtctctc atatttacac tttcattgtt tagtagatac ttctaagtcc caaatgtgtg    8040
ccccatcctg ggcctggcat tggccatctc aggatcaatg tagaacttttt gccagaggac    8100 catcttgagc aaaggcctgg gaatccacta agacttttg ggaaccattg aggtaaccag    8160
tgatgtagaa gggagactta aacagcagat atggctgaga gataacatta gaaagtaggc    8220
tagagacaga ttgtgagggg ccttgaatgc ccagcaacaa tgacttgacc tttatccttt    8280
tggcagtaag gagccattga aggattttt gttttgtttt ttgttttgt tttttttt      8340 tttgagacag agttttgctc ttgtcgccca ggctggaata ctgtggtgtg atctcagctc    8400
actgcaaccc cctcttccaa ggttcaagcg attccctgc cttagcctcc tgagtagctg    8460
ggattacagg tgcccaccac catgcccggc tactttttg tattttagt agagacaggg    8520 tttcaccatg ttggccaggc                                                8540

<210> SEQ ID NO 2
<211> LENGTH: 166
<212> TYPE: DNA
<213> ORGANISM: Homo sapiens
```

-continued

<400> SEQUENCE: 2
gcgttcccaa ggacaggctg ggcttctgag gaagttgccc accctctcgg aatctggttt    60
ggcctccgta aaatgggcag atcccgctcg gatggcccgg ttcccggctt ccttttgcgg    120
gtcaacggca gcgtcacgcg cgcgagcgcg gtctgcaaag cccca                    166

<210> SEQ ID NO 3
<211> LENGTH: 83
<212> TYPE: DNA
<213> ORGANISM: Homo sapiens

<400> SEQUENCE: 3
gcgctgggcg tcacgcgggg attgctgtcg ccgctgccag ccgcagcagc gacgcgaact    60
cggggcgccc ggcccgggcg cgc                                            83

<210> SEQ ID NO 4
<211> LENGTH: 261
<212> TYPE: DNA
<213> ORGANISM: Homo sapiens

<400> SEQUENCE: 4
gggggcgggg acgcgcacgc ggcgagggcg gcgggtgcga cggggcggg gacggggcg      60 gggacggggg cgaaggggc ggggacgggg gcgccccggc ctaagcggga ctaggagggc    120
gcgccacccg cttccgctgc ccgccgggga atccccgggg ctggcgcgca gggaagttcc    180
cgaacgcgcg ggcataaaag gcagccggc gcccgcgcgc cacagctctg cagctcgtgg    240
cagcggcgca gcgctccagc c                                             261

<210> SEQ ID NO 5
<211> LENGTH: 185
<212> TYPE: DNA
<213> ORGANISM: Homo sapiens

<400> SEQUENCE: 5
cctatgggtg atgcaaaacg aaagaggata tatggtgtca tctctgggtg atgctgcggg    60
ggtgaggaga gtgaagcatc acaagacaag tgcccttttc agatgatttc caaaggaagg    120
gagaaaaggg aagtaagagt gtgacttcat ataaaagtct actataaata gactttataa    180
tattg                                                                185

<210> SEQ ID NO 6
<211> LENGTH: 37
<212> TYPE: DNA
<213> ORGANISM: Artificial
<220> FEATURE:
<223> OTHER INFORMATION: Primer

<400> SEQUENCE: 6
ggcggtacca gctgggctc ttctcaatat tataaag                              37

<210> SEQ ID NO 7
<211> LENGTH: 32
<212> TYPE: DNA
<213> ORGANISM: Artificial
<220> FEATURE:
<223> OTHER INFORMATION: Primer

<400> SEQUENCE: 7
ggcggtacca gatgatttcc aaaggaaggg ag                                  32

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
ggcggtaccc aatattataa agtctattta tag                33

<210> SEQ ID NO 9
<211> LENGTH: 31
<212> TYPE: DNA
<213> ORGANISM: Artificial
<220> FEATURE:
<223> OTHER INFORMATION: Primer

<400> SEQUENCE: 9
ggcggtacca ggtgccaatg gggacagtac g                  31

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
ggcggtacca gaaggcattg caactctgg                     29

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
ggcggtaccg atgcttcact ctcctcacc                     29

<210> SEQ ID NO 12
<211> LENGTH: 34
<212> TYPE: DNA
<213> ORGANISM: Artificial
<220> FEATURE:
<223> OTHER INFORMATION: Primer

<400> SEQUENCE: 12
ggcggtacca gtactttggg cctggttgat aatc               34

<210> SEQ ID NO 13
<211> LENGTH: 33
<212> TYPE: DNA
<213> ORGANISM: Artificial
<220> FEATURE:
<223> OTHER INFORMATION: Primer

<400> SEQUENCE: 13
ggcggtaccc ctatgggtga tgcaaaacga aag                33

<210> SEQ ID NO 14
<211> LENGTH: 34
<212> TYPE: DNA
<213> ORGANISM: Artificial
<220> FEATURE:
<223> OTHER INFORMATION: Primer

```
<400> SEQUENCE: 14
ccagggtacc gaggaggtat tttgagaaaa tatg                                34

<210> SEQ ID NO 15
<211> LENGTH: 38
<212> TYPE: DNA
<213> ORGANISM: Artificial
<220> FEATURE:
<223> OTHER INFORMATION: Primer

<400> SEQUENCE: 15
ccagggtacc acaatatcat gtctgtgagg agtaaagc                            38

<210> SEQ ID NO 16
<211> LENGTH: 29
<212> TYPE: DNA
<213> ORGANISM: Artificial
<220> FEATURE:
<223> OTHER INFORMATION: Primer

<400> SEQUENCE: 16
ggcggtacct ataatattga gaagagccc                                      29

<210> SEQ ID NO 17
<211> LENGTH: 29
<212> TYPE: DNA
<213> ORGANISM: Artificial
<220> FEATURE:
<223> OTHER INFORMATION: Primer

<400> SEQUENCE: 17
ggcggtacca ttggcaccta tagtacttg                                      29

<210> SEQ ID NO 18
<211> LENGTH: 29
<212> TYPE: DNA
<213> ORGANISM: Artificial
<220> FEATURE:
<223> OTHER INFORMATION: Primer

<400> SEQUENCE: 18
ggcggtaccc ttacgcctgt aatcccagc                                      29

<210> SEQ ID NO 19
<211> LENGTH: 30
<212> TYPE: DNA
<213> ORGANISM: Artificial
<220> FEATURE:
<223> OTHER INFORMATION: Primer

<400> SEQUENCE: 19
gcagggtacc ttcctcttct ttgtgtagtg                                     30

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
ttaaggtacc gtaggtgctg cgatacc                                        27

<210> SEQ ID NO 21
```

```
<211> LENGTH: 31
<212> TYPE: DNA
<213> ORGANISM: Artificial
<220> FEATURE:
<223> OTHER INFORMATION: Primer

<400> SEQUENCE: 21
ccggggtacc aatgaagtag gaatatttaa c                              31

<210> SEQ ID NO 22
<211> LENGTH: 31
<212> TYPE: DNA
<213> ORGANISM: Artificial
<220> FEATURE:
<223> OTHER INFORMATION: Primer

<400> SEQUENCE: 22
cattggtacc ttacttactg tgggatcaga g                              31

<210> SEQ ID NO 23
<211> LENGTH: 32
<212> TYPE: DNA
<213> ORGANISM: Artificial
<220> FEATURE:
<223> OTHER INFORMATION: Primer

<400> SEQUENCE: 23
gcaaggtacc aaagaaccac atctattaca ac                             32

<210> SEQ ID NO 24
<211> LENGTH: 46
<212> TYPE: DNA
<213> ORGANISM: Artificial
<220> FEATURE:
<223> OTHER INFORMATION: Primer

<400> SEQUENCE: 24
ggcggtaccc ctatgggtga tgcaggacta tagaggatat atggtg              46

<210> SEQ ID NO 25
<211> LENGTH: 46
<212> TYPE: DNA
<213> ORGANISM: Artificial
<220> FEATURE:
<223> OTHER INFORMATION: Primer

<400> SEQUENCE: 25
ggcggtaccc ctatgggtga tgcaaaacga aagaggatat atggtg              46

<210> SEQ ID NO 26
<211> LENGTH: 76
<212> TYPE: DNA
<213> ORGANISM: Artificial
<220> FEATURE:
<223> OTHER INFORMATION: Primer

<400> SEQUENCE: 26
ggcggtaccc aatattataa agtctatttta tagtagactt ttatatgaag tcacactctt   60
attcctctcc tctccc                                               76

<210> SEQ ID NO 27
<211> LENGTH: 76
<212> TYPE: DNA
<213> ORGANISM: Artificial
<220> FEATURE:
<223> OTHER INFORMATION: Primer
```

<400> SEQUENCE: 27

```
ggcggtaccc aatattataa agtctatttta tagtagactt ttatatgaag tcacactctt      60
acttcccttt tctccc                                                      76
```

<210> SEQ ID NO 28
<211> LENGTH: 1271
<212> TYPE: DNA
<213> ORGANISM: Artificial
<220> FEATURE:
<223> OTHER INFORMATION: Promoter region of vector pGL3/-510/S1/Es

<400> SEQUENCE: 28

```
tgcagacatt tctctatcga taggtacccc tatgggtgat gcaaaacgaa agaggatata      60
tggtgtcatc tctgggtgat gctgcggggg tgaggagagt gaagcatcac aagacaagtg     120
cccttttcag atgatttcca aggaaggga gaaaagggaa gtaagagtgt gacttcatat     180
aaaagtctac tataaataga ctttataata ttgggtaccg agctcgaata atatgttcaa     240
gtgctgagaa ggaataaccg tcaacttaca actacactat gattcaagga tatgggcaaa     300
ataaacactt tcacacaaaa acagagagca ttttccactt gaagaccttt gctaaaagaa     360
ttaacaatat acttcagaag gaattgaacc aagaagaag cagtgagatg tacaatatga     420
gataaatttc aacaaatatc taatatgtaa aaaaagacta cttggggagt ataaaaacat     480
agtggaacaa gggtactggt cataatagta gatgagatgg gcagagttcg ggcatttggg     540
cattttaggg caaagggtgg caatattaat taactctaga atttattaaa tcgagtatgc     600
ttatgaaaaa ttataaaaag ttaatcacat aagaagagaa atagtatgca tgacttccaa     660
accagtagag agaacaccac agaatatata tttctattttt tattttattt tttgagacca     720
agtctggctc tgttgccacg cgtgctagcg cgttcccaag gacaggctgg gcttctgagg     780
aagttgccca ccctctcgga atctggtttg gcctccgtaa aatgggcaga tcccgctcgg     840
atggcccggt tcccggcttc cttttgcggg tcaacggcag cgtcacgcgc gcgagcgcgg     900
tctgcaaagc ccccagcgct gggcgtcacg cggggattgc tgtcgccgct gccagccgca     960
gcagcgacgc gaactcgggg cgcccggccc gggcgcgcgg gggcggggac gcgcacgcgg    1020
cgagggcggc gggtgcgacg ggggcgggga cggggcggg gacggggcg aaggggcgg    1080
ggacgggggc gccccggcct aagcgggact aggagggcgc gccacccgct tccgctgccc    1140
gccgggaat cccccgggct ggcgcgcagg gaagttcccg aacgcgcggg cataaaaggg    1200
cagccggcgc ccgcgcgcca cagctctgca gctcgtggca gcggcgcagc gctccagccc    1260
tcgagatctg c                                                         1271
```

<210> SEQ ID NO 29
<211> LENGTH: 1269
<212> TYPE: DNA
<213> ORGANISM: Artificial
<220> FEATURE:
<223> OTHER INFORMATION: promoter region of vector pGL3/-510/S1/Eas

<400> SEQUENCE: 29

```
cagacatttc tctatcgata ggtacccaat attataaagt ctatttatag tagactttta      60
tatgaagtca cactcttact tcccttttct cccttccttt ggaaatcatc tgaaaagggc     120
acttgtcttg tgatgcttca ctctcctcac ccccgcagca tcaccagag atgacaccat     180
atatcctctt tcgttttgca tcacccatag gggtaccgag ctcgaataat atgttcaagt     240
```

```
                                         -continued
gctgagaagg aataaccgtc aacttacaac tacactatga ttcaaggata tgggcaaaat    300
aaacactttc acacaaaaac agagagcatt ttccacttga agacctttgc taaaagaatt    360
aacaatatac ttcagaagga attgaaccaa gaaagaagca gtgagatgta caatatgaga    420
taaatttcaa caaatatcta atatgtaaaa aaagactact tggggagtat aaaaacatag    480
tggaacaagg gtactggtca taatagtaga tgagatgggc agagttcggg catttgggca    540
ttttagggca aagggtggca atattaatta actctagaat ttattaaatc gagtatgctt    600
atgaaaaatt ataaaaagtt aatcacataa gaagagaaat agtatgcatg acttccaaac    660
cagtagagag aacaccacag aatatatatt tctatttta ttttattttt tgagaccaag    720
tctggctctg ttgccacgcg tgctagcgcg ttcccaagga caggctgggc ttctgaggaa    780
gttgcccacc ctctcggaat ctggtttggc ctccgtaaaa tgggcagatc ccgctcggat    840
ggcccggttc ccggcttcct tttgcgggtc aacggcagcg tcacgcgcgc gagcgcggtc    900
tgcaaagccc ccagcgctgg gcgtcacgcg gggattgctg tcgccgctgc cagccgcagc    960
agcgacgcga actcggggcg cccggcccgg gcgcgcgggg gcggggacgc gcacgcggcg   1020
agggcggcgg gtgcgacggg ggcggggacg ggggcgggga cgggggcgaa ggggcgggg    1080 acggggcgc cccggcctaa gcgggactag gagggcgcgc cacccgcttc cgctgcccgc    1140
cggggaatcc cccgggctgg cgcgcaggga agttcccgaa cgcgcgggca taaaagggca   1200
gccggcgccc gcgcgccaca gctctgcagc tcgtggcagc ggcgcagcgc tccagccctc   1260
gagatctgc                                                           1269
```